(12) United States Patent
Gudmundsson et al.

(10) Patent No.: US 7,153,863 B2
(45) Date of Patent: Dec. 26, 2006

(54) THERAPEUTIC COMPOUNDS BASED ON PYRAZOLOPYRIDLINE DERIVATIVES

(75) Inventors: Kristjan S Gudmundsson, Durham, NC (US); Brian A Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/530,101

(22) PCT Filed: Sep. 24, 2003

(86) PCT No.: PCT/US03/30334

§ 371 (c)(1),
(2), (4) Date: Apr. 1, 2005

(87) PCT Pub. No.: WO2004/033454

PCT Pub. Date: Apr. 22, 2004

(65) Prior Publication Data

US 2005/0282842 A1    Dec. 22, 2005

Related U.S. Application Data

(60) Provisional application No. 60/415,939, filed on Oct. 3, 2002.

(51) Int. Cl.
C07D 471/04 (2006.01)
C07D 401/04 (2006.01)
A61K 31/4353 (2006.01)
A61K 31/506 (2006.01)
A61P 31/22 (2006.01)

(52) U.S. Cl. .............. 514/274; 514/275; 544/316; 544/331

(58) Field of Classification Search .......... 544/316, 544/331; 514/274, 275
See application file for complete search history.

(56) References Cited

U.S. PATENT DOCUMENTS

| | | |
|---|---|---|
| 4,576,952 A | 3/1986 | Hurst et al. |
| 4,621,089 A | 11/1986 | Ward et al. |
| 4,670,432 A | 6/1987 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,773,530 A | 6/1998 | Akahane et al. |
| 5,990,148 A | 11/1999 | Isakson et al. |
| 6,136,839 A | 10/2000 | Isakson et al. |
| 6,207,675 B1 | 3/2001 | Carry et al. |

FOREIGN PATENT DOCUMENTS

| | | |
|---|---|---|
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| WO | EP 0 364 204 A1 | 10/1989 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41626 | 12/1996 |
| WO | WO 96 41645 | 12/1996 |
| WO | WO 96 41625 | 12/1997 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01/014375 | 3/2001 |
| WO | WO 01 14375 | 3/2001 |
| WO | WO 02 16359 | 2/2002 |

(Continued)

OTHER PUBLICATIONS

Wolft Manfréd E. "Burger's Medicinal Chemistry, 5ed, Part 1", John Wiley & Sons, 1995, pp. 975-977.*
Banker, G. S. et al, "Modern Pharmaceutics, 3ed. ", Marcel Dekker, New York. 1996, pp. 451 and 596.*

(Continued)

Primary Examiner—James O. Wilson
Assistant Examiner—Venkataraman Balasubramanian
(74) Attorney, Agent, or Firm—Lorie Ann Morgan

(57) ABSTRACT

The present invention provides compounds of formula (I):

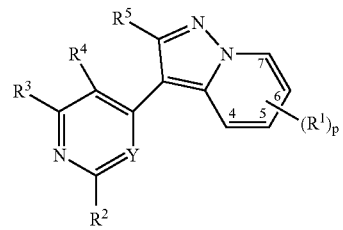

wherein all variables are as defined herein, pharmaceutical compositions containing the same, processes for preparing the same and their use as pharmaceutical agents.

17 Claims, No Drawings

FOREIGN PATENT DOCUMENTS

| | | |
|---|---|---|
| WO | WO 02 18382 | 3/2002 |
| WO | WO 02/48147 | 6/2002 |
| WO | WO 02 48147 | 6/2002 |
| WO | WO 02/048148 | 6/2002 |
| WO | WO 02/48148 | 6/2002 |
| WO | WO 02 066481 | 8/2002 |
| WO | WO 02/072581 | 9/2002 |
| WO | WO 03/00682 | 1/2003 |

OTHER PUBLICATIONS

West, Anthony R., Solid State Chemistry and its Applications, Wiley, New York, 1988, pp. 358 and 365.*
Vippagunta et al., Advanced Drug Delivery Reviews 48: 3-26, 2001.*
Bosseray et al., Pathol. Biol. (Paris) 50(8); 483-492, 2002.*
Razonable et al., Herpes. 10(3): 60-65, 2003.*
Vane, J. et al. "Towards a Better Aspirin." Nature, vol. 367, Jan. 20, 1994, pp. 215-216.
Carter, J. et al. "Recently Reported Inhibitors of Cyclooxygenase-2." Exp. Opin. Ther. Patents (1998), 8(1), pp. 21-29.
Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.
Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.
Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.
Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.
Talley, John J., 5 Selective Inhibitors of Cyclooxygenase-2 (COX-2) *Progress in Medicinal Chemistry*, vol. 36, (1999): pp. 201-234.
Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.
Hanson, G.J., et al. "Pulmonary-Allergy, Dermatological, Gastrointestinal & Arthritis, Inhibitors of p38 kinase." Expert Opinion Ther. Patents, 1997, 7(7):729-733.
Roizman, B., et al. "The Family Herpesviridae: A Brief Introduction." Fields Virology, vol. 2, 4th Edition, pp. 2381-2397.
Douglas, R.G., Jr. "Introduction to Viral Diseases." Cecil Textbook of Medicine, 20th Edition, vol. 2, pp. 1739-1747, 1996.
Razonable, R.R., et al. "Herpes Virus Infections in Transplant Recipients: Current Challenges in the Clinical Management of Cytomegalovirus and Epstein-Barr Virus Infections." PubMed Abstract, Herpes 10(3):60-5, Dec. 2003.
Bosseray; A., et al. "What's New in Vaccines Against Herpes Simplex Infections." PubMed Abstract, Pathol. Biol (Paris) 50(*):483-92, Oct. 2002.
Sekine, T., et al. Cardioprotective Effects and Pluorescence Profiles of AHC-93, A Novel Dihydropyridine Compound with C1 Current Blocking Activity. Research Communications in Pharmacology and Toxicology, vol.-3, Nos. 1 & @, 1998, pp. 1-10.
Takahashi, M., et al. "Role of P-Glycoprotein in Human Natural Killer-Like Cell Line-Mediated Cytotoxicity." Experimental Cell Research, 1999, vol. 253, pp. 396-402.

* cited by examiner

THERAPEUTIC COMPOUNDS BASED ON PYRAZOLOPYRIDLINE DERIVATIVES

CROSS REFERENCES TO RELATED APPLICATIONS

This application is a 371 Application of PCT/US03/030334, filed 24 Sep. 2003, which claims priority to U.S. application Ser. No. 60/415,939, filed 3 Oct. 2002.

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group cause the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varicella zoster virus (VZV) (also known as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular, fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin's lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

U.S. Pat. No. 5,498,774 and European Patent No. 0 404 190 to Mitsudera et al., relates to condensed heterocyclic compounds of the formula (I):

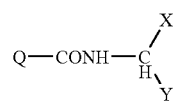

wherein Q is a condensed heterocyclic group having a nitrogen atom in the bridgehead which is unsubstituted or substituted, X is a hydrogen atom or a group bonded through C, O, S or N, and Y is an electron attractive group; or its salt which is useful as an agricultural chemical.

BRIEF SUMMARY OF THE INVENTION

The present invention provides a compound of formula (I):

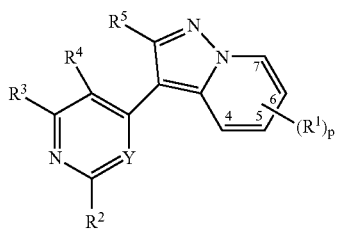

wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Ay, —C(O)$NHR^{10}$Het, —C(S)$NR^9R^{11}$, —C(NH)$NR^7R^8$, —C(NH)$NR^7$Ay, —S(O)$_nR^9$, —S(O)$_n$Ay, —S(O)$_n$Het, —S(O)$_2NR^7R^8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—C(O)$R^9$, —$R^{10}$O—C(O)Ay, —$R^{10}$O—C(O)Het, —$R^{10}$O—S(O)$_nR^9$, —$R^{10}OR^9$, —$R^{10}$C(O)$R^9$, —$R^{10}CO_2R^9$, —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}SO_nR^9$, —$R^{10}SO_2NR^9R^{11}$, —$R^{10}SO_2NHCOR^9$, —$R^{10}NR^7R^8$, —$R^{10}NR^7$Ay, —$R^{10}$NHC(NH)$NR^9R^{11}$, cyano, nitro and azido; or
two adjacent $R^1$ groups together with the atoms to which they are bonded form a $C_{5-6}$cycloalkyl or a 5 or 6-membered heterocyclic ring containing 1 or 2 heteroatoms;
each $R^7$ and $R^8$ are the same or different and are independently selected from the group consisting of H, alkyl, alkenyl, cycloalkyl, cycloalkenyl, —C(O)$R^9$, —$CO_2R^9$, —C(O)$NR^9R^{11}$, —C(S)$NR^9R^{11}$, —C(NH)$NR^9R^{11}$, —$SO_2R^{10}$, —$SO_2NR^9R^{11}$, —$R^{10}$cycloalkyl, —$R^{10}OR^9$, —$R^{10}$C(O)$R^9$, —$R^{10}CO_2R^9$, —$R^{10}$C(O)$NR^9R^{11}$, —$R^{10}$C(S)$NR^9R^{11}$, —$R^{10}$C(NH)$NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}$ $NHCOR^9$, —$R^{10}NHSO_2R^9$ and —$R^{10}$NHC(NH)$NR^9R^{11}$;
each $R^9$ and $R^{11}$ are the same or different and are independently selected from the group consisting of H, alkyl, cycloalkyl, —$R^{10}$cycloalkyl, —$R^{10}$OH, —$R_{10}$(OR$^{10}$)$_w$ where w is 1–10, and —$R^{10}NR^{10}R^{10}$;
each $R^{10}$ is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
$R^2$ is selected from the group consisting of halo, alkyl, alkenyl, cycloalkyl, cycloalkenyl, Ay, Het, —$OR^7$, —OAy, —OHet, —$OR^{10}$Het, —S(O)$_nR^9$, —S(O)$_n$Ay, —S(O)$_nNR^7R^8$, —S(O)$_n$Het, —$NR^7R^8$, —NHHet, —$NHR^{10}$Ay, —$NHR^{10}$Het, —$R^{10}NR^7R^8$ and —$R^{10}NR^7$Ay;
n is 0, 1 or 2;
Y is N or CH;
$R^3$ and $R^4$ are the same or different and are each independently selected from the group consisting of H, halo, alkyl, alkenyl, cycloalkyl, Ay, Het, —$OR^7$, —OAy, —C(O)$R^7$, —C(O)Ay, —$CO_2R^7$, —$CO_2$Ay, —$SO_2NHR^9$, —$NR^7R^8$, —$NR^7$Ay, —NHHet, —$NHR^{10}$Het, —$R^{10}$cycloalkyl, —$R^{10}OR^7$, —$R^{10}$Ay, —$R^{10}NR^7R^8$ and —$R^{10}NR^7$Ay;
$R^5$ is the selected from the group consisting of H, halo, alkyl, alkenyl, alkynyl, cycloalkyl, cycloalkenyl, —$OR^7$, —OAy, —OHet, —$OR^{10}$Ay, —$OR^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Het, —CH(OR$^9$)$_2$, —CH(OR$^9$)—$R^{10}$, —CH(OR$^9$)—Ay, —C(S)$NR^9R^{11}$, —C(NH)$NR^7R^8$, —C(NH)$NR^7$Ay, —S(O)$_nR^9$, —S(O)$_2NR^7R^8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}OR^9$, —$R^{10}$C(O)$R^9$, —$R^{10}$C(O)Ay, —$R^{10}$C(O)Het, —$R^{10}CO_2R^9$, —$R^{10}$C(O)$NR^9R^{11}$, —$R^{10}$C(O)$NR^7$Ay, —$R^{10}$C(O)$NHR^{10}$Het, —$R^{10}$CH(OR$^9$)—$R^{10}$, —$R^{10}$CH(OR$^9$)—Ay, —$R^{10}$C(S)$NR^9R^{11}$, —$R^{10}$C(NH)$NR^9R^{11}$, —$R^{10}SO_nR^9$, —$R^{10}SO_2NR^9R^{11}$, —$R^{10}SO_2NHCOR^9$, —$R^{10}NR^7R^8$, —$R^{10}NR^7$Ay, —$R^{10}$NHC(NH)$NR^9R^{11}$, cyano, nitro and azido; or
wherein when Y is CH, $R^3$ is not —$NR^7$Ay;

or a pharmaceutically acceptable salt, solvate or physiologically functional derivative thereof.

The present invention also provides a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir, valaciclovir and pharmaceutically acceptable salts thereof.

The present invention also provides a method for the prophylaxis or treatment of a herpes viral infection in an animal. The method comprises administering a therapeutically effective amount of a compound of formula (I) or a pharmaceutically acceptable salt, solvate or physiologically functional derivative thereof. The herpes viral infection can be any of herpes simplex virus 1, herpes simplex virus 2, cytomegalovirus, Epstein Barr virus, varicella zoster virus, human herpes virus 6, human herpes virus 7, and human herpes virus 8.

The present invention also provides a method for the prophylaxis or treatment of a condition or disease associated with a herpes viral infection in an animal. The method comprises administering to the animal a therapeutically effective amount of the compound of formula (I) or a pharmaceutically acceptable salt, solvate or physiologically functional derivative thereof.

The present invention also provides a process for preparing a compound of formula (I). The process comprises the steps of:

a) coupling a compound of formula (II):

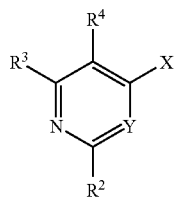

wherein X is chloro, bromo, iodo or triflate;
to a terminal alkyne of formula (III):

to prepare a compound of formula (IV):

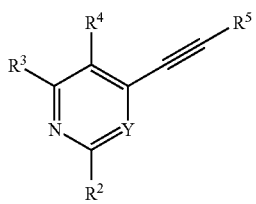

and
b) reacting an N-amino pyridinium salt of formula (V):

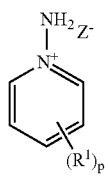

wherein Z- is a counterion;
with the compound of the formula (IV) to prepare a compound of formula (I).

The present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

The present invention provides a compound of formula (I) for use in therapy.

The present invention provides a compound of formula (I) for use in the prophylaxis or treatment of a herpes viral infection in an animal, particularly a human.

The present invention provides a compound of formula (I) for use in the prophylaxis or treatment of a condition or disease associated with a herpes viral infection in an animal, particularly a human.

The present invention provides the use of a compound of formula (I) for the preparation of a medicament for the prophylaxis or treatment of a herpes viral infection in an animal, particularly a human.

The present invention provides the use of a compound of formula (I) for the preparation of a medicament for the treatment or prophylaxis of a condition or disease associated with a herpes viral infection in an animal, particularly a human. The present invention also provides a pharmaceutical composition comprising a compound of formula (I) for use in the prophylaxis or treatment of a herpes viral infection in an animal, particularly a human.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolateable intermediates such as for example, compounds of formula (IV), the phrase "a compound of formula "(number)" means a compound having that formula and pharmaceutically acceptable salts, solvates and physiologically functional derivatives thereof.

As used herein, the terms "alkyl" (and alkylene) refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" and "alkylene" also include substituted alkyl and substituted alkylene. The alkyl groups may be optionally substituted with one or more substituents selected from the group consisting of mercapto, nitro, cyano and halo. Perhalo alkyl, such as trifluoromethyl is one particular alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl also includes substituted cycloalkyl. The cycloalkyl may be optionally substituted on any available carbon(s) with one or more substituents selected from the group consisting of mercapto, nitro, cyano, halo and alkyl.

As used herein, the term "alkenyl" refers to straight or branched hydrocarbon chains containing from 2 to 8 carbon atoms and at least one and up to three carbon-carbon double bonds. Examples of alkenyl as used herein include, but are not limited to ethenyl and propenyl. "Alkenyl" also includes substituted alkenyl. The alkenyl groups may optionally be substituted on any available carbon(s) with one or more substituents selected from the group consisting of mercapto, nitro, cyano, halo and alkyl.

As used herein, the term "cycloalkenyl" refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon(s) with one or more substituents selected from the group consisting of mercapto, nitro, cyano, halo and alkyl.

As used herein, the term "alkynyl" refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted on any available carbon(s) with one or more substituents selected from the group consisting of mercapto, nitro, cyano, halo and alkyl.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms (unless otherwise specified) and having at least one aromatic ring. Examples of particular aryl groups include but are not limited to phenyl, and naphthyl. "Aryl" also includes substituted aryl. Aryl groups may optionally be substituted on any available carbon(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred aryl groups according to the invention include but are not limited to phenyl and substituted phenyl.

The term "heterocyclic" (or "heterocycle") refers to monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic groups may optionally be substituted on any available carbon(s) or heteroatom(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred heterocyclic groups according to the invention include but are not limited to pyrrolidine, piperidine, morpholine, thiomorpholine and piperazine, and substituted variants thereof.

The term "heteroaryl" refers to aromatic monocyclic groups and aromatic fused bicyclic groups (wherein at least one ring is aromatic) having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl groups may optionally be substituted on any available carbon(s) or heteroatom(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred heteroaryl groups according to the invention include but are not limited to pyridine, furan, thiophene, pyrrole, imidazole, pyrazole, and pyrimidine, and substituted variants thereof.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula formula (I):

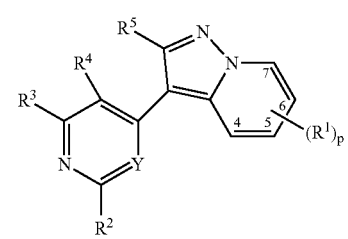

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, $-OR^7$, $-OAy$, $-OR^{10}Ay$, $-OHet$, $-OR^{10}Het$, $-C(O)R^9$, $-C(O)Ay$, $-C(O)Het$, $-CO_2R^9$, $-C(O)NR^7R^8$, $-C(O)NR^7Ay$, $-C(O)NHR^{10}Ay$, $-C(O)NHR^{10}Het$, $-C(S)NR^9R^{11}$, $-C(NH)NR^7R^8$, $-C(NH)NR^7Ay$, $-S(O)_nR^9$, $-S(O)_nAy$, $-S(O)_nHet$, $-S(O)_2NR^7R^8$, $-S(O)_2NR^7Ay$, $-NR^7R^8$, $-NR^7Ay$, $-NHHet$, $-NHR^{10}Ay$, $-NHR^{10}Het$, $-R^{10}$cycloalkyl, $-R^{10}Ay$, $-R^{10}Het$, $-R^{10}O-C(O)R^9$, $-R^{10}O-C(O)Ay$, $-R^{10}O-C(O)Het$, $-R^{10}O-S(O)_nR^9$, $-R^{10}OR^9$, $-R^{10}C(O)R^9$, $-R^{10}CO_2R^9$, $-R^{10}C(O)NR^9R^{11}$, $-R^{10}C(O)NR^7Ay$, $-R^{10}C(O)NHR^{10}Het$, $-R^{10}C(S)NR^9R^{11}$, $-R^{10}C(NH)NR^9R^{11}$, $-R^{10}SO_nR^9$, $-R^{10}SO_2NR^9R^{11}$, $-R^{10}SO_2NHCOR^9$, $-R^{10}NR^7R^8$, $-R^{10}NR^7Ay$, $-R^{10}NHC(NH)NR^9R^{11}$, cyano nitro and azido; or two adjacent $R^1$ groups together with the atoms to which they are bonded form a $C_{5-6}$cycloalkyl or a 5 or 6-membered heterocyclic ring containing 1 or 2 heteroatoms;

each $R^7$ and $R^8$ are the same or different and are independently selected from the group consisting of H, alkyl, alkenyl, cycloalkyl, cycloalkenyl, $-C(O)R^9$, $-CO_2R^9$, $-C(O)NR^9R^{11}$, $-C(S)NR^9R^{11}$, $-C(NH)NR^9R^{11}$, $-SO_2R^{10}$, $-SO_2NR^9R^{11}$, $-R^{10}$cycloalkyl, $-R^{10}OR^9$, $-R^{10}C(O)R^9$, $-R^{10}CO_2R^9$, $-R^{10}C(O)NR^9R^{11}$, $-R^{10}C(S)NR^9R^{11}$, $-R^{10}C(NH)NR^9R^{11}$, $-R^{10}SO_2R^{10}$, $-R^{10}SO_2NR^9R^{11}$, $-R^{10}SO_2NHCOR^9$, $-R^{10}NR^9R^{11}$, $-R^{10}NHCOR^9$, $-R^{10}NHSO_2R^9$ and $-R^{10}NHC(NH)NR^9R^{11}$;

each $R^9$ and $R^{11}$ are the same or different and are independently selected from the group consisting of H, alkyl, cycloalkyl, $-R^{10}$cycloalkyl, $-R^{10}OH$, $-R^{10}(OR^{10})_w$ where w is 1–10, and $-R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

$R^2$ is selected from the group consisting of halo, alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay;

n is 0, 1 or 2;

Y is N or CH;

$R^3$ and $R^4$ are the same or different and are each independently selected from the group consisting of H, halo, alkyl, alkenyl, cycloalkyl, Ay, Het, —$OR^7$, —OAy, —$C(O)R^7$, —C(O)Ay, —$CO_2R^7$, —$CO_2$Ay, —$SO_2NHR^9$, —$NR^7R^8$, —$NR^7$Ay, —NHHet, —$NHR^{10}$Het, —$R^{10}$cycloalkyl, —$R^{10}OR^7$, —$R^{10}$OAy, —$R^{10}NR^7R^8$ and —$R^{10}NR^7$Ay;

$R^5$ is the selected from the group consisting of H, halo, alkyl, alkenyl, alkynyl, cycloalkyl, cycloalkenyl, —$OR^7$, —OAy, —OHet, —$OR^{10}$Ay, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Het, —$CH(OR^9)_2$, —$CH(OR^9)$—$R^{10}$; —$CH(OR^9)$—Ay, —$C(S)NR^9R^{11}$, —$C(NH)NR^7R^8$, —$C(NH)NR^7$Ay, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}OR^9$, —$R^{10}C(O)R^9$, —$R^{10}C(O)$Ay, —$R^{10}C(O)$Het, —$R^{10}CO_2R^9$, —$R^{10}C(O)NR^9R^{11}$, —$R^{10}C(O)NR^7$Ay, —$R^{10}C(O)NHR^{10}$Het, —$R^{10}CH(OR^9)$—$R^{10}$; —$R^{10}CH(OR^9)$—Ay, —$R^{10}C(S)NR^9R^{11}$, —$R^{10}C(NH)NR^9R^{11}$, —$R^{10}SO_nR^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or wherein when Y is CH, $R^3$ is not —$NR^7$Ay;

or a pharmaceutically acceptable salt, solvate or physiologically functional derivative thereof.

In one particular class of compounds of formula (I), p is 0, 1, 2 or 3. In another embodiment, p is 0, 1, or 2. In one particular embodiment, p is 0 or 1. In one particular embodiment p is 0. In another particular embodiment p is 1. In one embodiment, p is 2 and optionally, two adjacent $R^1$ groups together with the atoms which they are bonded, form a $C_{5-6}$ cycloalkyl or 5- or 6-membered heterocyclic group. The phrase "two adjacent $R^1$ groups" refers to two $R^1$ groups, each bonded to adjacent carbon atoms on the pyrazolopyridine ring. In the embodiment where two adjacent $R^1$ groups together with the atoms to which they are bonded form a cycloalkyl or heterocyclic group, p is typically 2, 3 or 4; more typically 2.

$R^1$ may be in the 4, 5, 6 or 7 position. In one embodiment, p is 1 or more and $R^1$ is in the C-7 position. In one embodiment, p is 1 or more and $R^1$ is in the C-5 position. In one embodiment p is 2 or more and one $R^1$ is in the C-5 position and one $R^1$ is in the C-7 position.

In the embodiments where two adjacent $R^1$ groups together with the atoms to which they are bonded form a $C_{5-6}$cycloalkyl or 5- or 6-membered heterocyclic group having 1 or 2 heteroatoms, each $R^1$ group may be the same or different and is typically selected from the group consisting of alkyl, alkenyl, —$OR^7$, —$S(O)_nR^9$ and —$NR^7R^8$. For example, in one embodiment two adjacent $R^1$ groups are —$OR^7$ and together with the atoms to which they are bonded, they form a heterocyclic group such as:

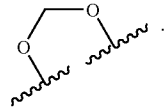

In another embodiment, two adjacent $R^1$ groups are alkyl and together with the atoms to which they are bonded, they form a cycloalkyl group such as:

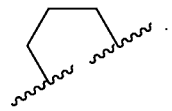

In another embodiment two adjacent $R^1$ groups are defined as —$OR^7$ and —$NR^7R^8$, respectively and together with the atoms to which they are bonded, they form a heterocyclic group such as:

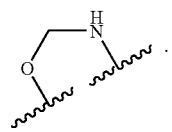

From these examples, additional embodiments can be readily ascertained by those skilled in the art In one embodiment, two adjacent $R^1$ groups together with the atoms to which they are bonded do not form a $C_{5-6}$cycloalkyl or a 5 or 6-membered heterocyclic ring containing 1 or 2 heteroatoms.

In one embodiment, each $R^1$ is the same or different and is independently selected from the group consisting of halo, alkyl, cycloalkyl, Ay, Het, —$OR^7$, —$C(O)R^9$, —C(O)Het, —$CO_2R^9$, —$C(O)NR^7R^8$, —$C(O)NR^7$Ay, —$C(O)NHR^{10}$Het, —$S(O)_nR^9$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)NR^7$Ay, —$R^{10}SO_2NHCOR^9$, —$R^{10}NR^7R^8$, —$R^{10}NR^7$Ay, cyano, nitro and azido, or any subset thereof. More particularly, each $R^1$ is the same or different and is independently selected from the group consisting of halo, alkyl, Ay, Het, —$OR^7$, —$S(O)_nR^9$, —$NR^7R^8$, —$NR^7$Ay, —NHHet, —$NHR^{10}$Ay and —$NHR^{10}$Het. In one particular embodiment, each $R^1$ is the same or different and is independently selected form the group consisting of halo, alkyl, Ay, Het, —$OR^7$, —$S(O)_nR^9$, —$NR^7R^8$, —$NR^7$Ay, —NHHet and —$NHR^{10}$Het, or any subset thereof. Particular compounds of formula (I) are defined wherein each $R^1$ is the same or different and is independently selected from the group consisting of halo, Ay, Het, —$NR^7R^8$ and —$NR^7$Ay, or any subset thereof. In one embodiment, each $R^1$ is the same or different and is —$NR^7R^8$.

More specific examples of embodiments of the present invention are defined wherein each $R^1$ is the same or different and is independently selected from the group consisting of halo, phenyl, Het (and substituted Het), —O-alkyl, —S-alkyl, —$NH_2$, —NHalkyl, —NHcycloalkyl, —N(alkyl)(alkyl), —NHalkyl-OH, —NHalkyl-O-alkyl, —NHAy, and —NH-alkyl-Het, or any subset thereof. Specific examples of some particular $R^1$ groups are selected from the group consisting of Br, Cl, phenyl, —NH-methyl, —NH-butyl, —N(CH$_3$)$_2$, —NH-cyclopentyl, —NH-cyclopropyl, —NH-isopropyl, —NH-phenyl, —NH(CH$_2$)$_2$OCH$_3$, pyrrolidine, and morpholine, or any subset thereof.

In one embodiment, $R^2$ is selected from the group consisting of halo, alkenyl, cycloalkyl, cycloalkenyl, Ay, Het, —OR$^7$, —OAy, —OHet, —OR$^{10}$Het, —S(O)$_n$R$^9$, —NR$^7$R$^8$, —NHHet, —NHR$^{10}$Het, —R$^{10}$NR$^7$R$^8$ and —R$^{10}$NR$^7$Ay, or any subset thereof. In particular, $R^2$ is selected from the group consisting of halo, Het, —S(O)$_n$R$^9$, —NR$^7$R$^8$, —NHHet and —NHR$^{10}$Het, or any subset thereof. More particularly, $R^2$ is selected from the group consisting of —NR$^7$R$^8$, Het, —NHR$^{10}$Het and —NHHet, or any subset thereof. In one particular embodiment, compounds of formula (I) are defined where $R^2$ is —NR$^7$R$^8$.

Specific examples of embodiments of the present invention are defined wherein $R^2$ is selected from the group consisting of —NH$_2$, —NH-alkyl, —NH-cycloalkyl, Het, —NHHet and —NH-alkyl-Het, or any subset thereof. Particular embodiments include those compounds of formula (I) wherein $R^2$ is —NH$_2$, —NH-propyl, —NH-isopropyl, —NH-cyclopropyl, —NH-butyl, —NH-isobutyl, —NH-cyclobutyl, —NH-cyclopentyl, —NH-cyclohexyl, —NH(CH$_2$)$_2$OCH$_3$, pyrrolidine (e.g., pyrrolidine bonded through N), and morpholine (e.g., morpholine bonded through N), or any subset thereof.

In one embodiment, $R^7$ and $R^8$ are each the same or different and are independently selected from the group consisting of H, alkyl, cycloalkyl, —C(O)R$^9$, —R$^{10}$-cycloalkyl, —R$^{10}$OR$^9$, —R$^{10}$CO$_2$R$^9$ and R$^{10}$NR$^9$R$^{11}$, or any subset thereof. More particularly, $R^7$ and $R^8$ are each the same or different and are independently selected from the group consisting of H, alkyl, cycloalkyl, and —R$^{10}$-cycloalkyl, or any subset thereof. In one embodiment, $R^7$ and $R^8$ are each the same or different and are independently selected from the group consisting of H, alkyl and cycloalkyl.

The group —R$^{10}$(OR$^{10}$)$_w$ in the definition of $R^9$ and $R^{11}$ refers to an PEG-like chain such as alkyl-O-alkyl-O-alkyl. In one embodiment, $R^9$ and $R^{11}$ are each the same or different and are independently selected from the group consisting of H, alkyl, cycloalkyl, and —R$^{10}$-cycloalkyl, or any subset thereof. More particularly, $R^9$ and $R^{11}$ are each the same or different and are independently selected from the group consisting of H and alkyl.

In one embodiment, $R^{10}$ is alkyl or cycloalkyl; more particularly alkyl.

In one class of compounds of formula (I), Y is CH. In another class of compounds of formula (I), Y is N.

In one embodiment, $R^3$ is selected from the group consisting of H, halo, alkyl, Ay, —OR$^7$, —CO$_2$R$^7$, —NR$^7$R$^8$, —R$^{10}$OR$^7$ and —R$^{10}$NR$^7$R$^8$, or any subset thereof. More particularly, $R^3$ is selected from the group consisting of H, halo, alkyl, —OR$^7$, and —NR$^7$R$^8$, or any subset thereof. In one embodiment, $R^3$ is H or alkyl. In one embodiment $R^3$ is H.

In one embodiment, $R^4$ is selected from the group consisting of H, halo, alkyl, Ay, —OR$^7$, —CO$_2$R$^7$, —NR$^7$R$^8$, —R$^{10}$OR$^7$ and —R$^{10}$NR$^7$R$^8$, or any subset thereof. More preferably, $R^4$ is selected from the group consisting of H, halo, alkyl, —OR$^7$, and —NR$^7$R$^8$, or any subset thereof. In one embodiment, $R^4$ is H or alkyl. In one embodiment $R^4$ is H.

In one embodiment, $R^5$ is the selected from the group consisting of halo, alkyl, cycloalkyl, —OR$^7$, —C(O)R$^9$, —C(O)Ay, —C(O)Het, —CH(OR$^9$)—R$^{10}$, —CH(OR$^9$)—Ay, —S(O)$_n$R$^9$, —S(O)$_2$NR$^7$R$^8$, —NR$^7$R$^8$, —NR$^7$Ay, —R$^{10}$cycloalkyl, —R$^{10}$Ay, —R$^{10}$Het, —R$^{10}$OR$^9$, —R$^{10}$C(O)R$^9$, —R$^{10}$SO$_2$NR$^9$R$^{11}$ and —R$^{10}$NR$^7$R$^8$, or any subset thereof. More particularly, $R^5$ is selected from the group consisting of alkyl, cycloalkyl, —C(O)R$^9$, —C(O)Ay, —C(O)Het, —CH(OR$^9$)—Ay, —NR$^7$R$^8$, —R$^{10}$cycloalkyl, —R$^{10}$Ay, —R$^{10}$Het, —R$^{10}$OR$^9$ and —R$^{10}$NR$^7$R$^8$, or any subset thereof. In one embodiment, $R^5$ is selected from the group consisting of alkyl, —C(O)Ay, —CH(OR$^9$)—Ay, —R$^{10}$cycloalkyl, —R$^{10}$Ay, —R$^{10}$OR$^9$ and —R$^{10}$NR$^7$R$^8$, or any subset there of.

Specific examples of compounds of formula (I) are defined wherein $R^5$ is selected from the group consisting of alkyl (e.g., methyl, ethyl, propyl, isopropy and isobutyl), cyclopropyl, alkyl-OH, alkyl-O-alkyl, alkyl-O-alkyl-O-alkyl, C(O)-phenyl, C(O)-benzyl, benzyl, -alkyl-Het (e.g., —CH$_2$-morpholino and —CH$_2$-pyrrolidinyl), —N(H)alkyl, —N(alkyl)$_2$, -alkyl-N(H)alkyl, and -alkyl-N(alkyl)$_2$, or any subset thereof.

It is to be understood that the present invention includes all combinations and subsets of the particular and preferred groups defined hereinabove.

Specific examples of compounds of formula (I) include but are not limited to:

3-(2-Fluoropyridin-4-yl)-2-propylpyrazolo[1,5-a]pyridine;

N-Cyclopentyl-4-(2-propylpyrazolo[1,5-a]pyridin-3-yl)pyridin-2-amine;

7-Chloro-3-(2-fluoropyridin-4-yl)-2-propylpyrazolo[1,5-a]pyridine;

N-Cyclopentyl-3-[2-(cyclopentylamino)pyridin-4-yl]-2-propylpyrazolo[1,5-a]pyridin-7-amine;

2-Isobutyl-3-[2-(methylthio)pyrimidin-4-yl]pyrazolo[1,5-a]pyridine;

2-Isobutyl-3-[2-(methylsulfinyl)pyrimidin-4-yl]pyrazolo[1,5-a]pyridine;

N-Cyclopentyl-4-(2-isobutylpyrazolo[1,5-a]pyridin-3-yl)pyrimidin-2-amine;

N-Cyclopentyl-4-[2-isobutyl-7-(methylthio)pyrazolo[1,5-a]pyridin-3-yl]pyrimidin-2-amine;

N-Cyclopentyl-4-[2-isobutyl-7-(methylsulfinyl)pyrazolo[1,5-a]pyridin-3-yl]pyrimidin-2-amine;

N-Cyclopentyl-3-[2-(cyclopentylamino)pyrimidin-4-yl]-2-isobutylpyrazolo[1,5-a]pyridin-7-amine;

2-(Diethoxymethyl)-3-[2-(methylthio)pyrimidin-4-yl]pyrazolo[1,5-a]pyridine;

3-[2-(Methylthio)pyrimidin-4-yl]pyrazolo[1,5-a]pyridine-2-carbaldehyde;

{3-[2-(methylthio)pyrimidin-4-yl] pyrazolo[1,5-a]pyridin-2-yl}(phenyl)methanol;

{3-[2-(Cyclopentylamino)-4-pyrimidinyl]pyrazolo[1,5-a]pyridin-2-yl}(phenyl)methanol;

{3-[2-(Cyclopentylamino)-4-pyrimidinyl]pyrazolo[1,5-a]pyridin-2-yl}(phenyl)methanone;

{7-(Cyclopentylamino)-3-[2-(cyclopentylamino)-4-pyrimidinyl]pyrazolo[1,5-a]pyridin-2-yl}(phenyl)methanone;

4-(2-Benzylpyrazolo[1,5-a]pyridin-3-yl)-N-cyclopentyl-2-pyrimidinamine;

4-(2-Benzyl-7-chloropyrazolo[1,5-a]pyridin-3-yl)-N-cyclopentyl-2-pyrimidinamine;

N-{4-[2-Benzyl-7-(cyclopentylamino)pyrazolo[1,5-a]pyridin-3-yl]-2-pyrimidinyl}-N-cyclopentylamine;

N-Cyclopentyl-4-[2-(methoxymethyl)pyrazolo[1,5-a]pyridin-3-yl]-2-pyrimidinamine;

N-Cyclopentyl-4-[2-(methoxymethyl)-7-(methylsulfanyl) pyrazolo[1,5-a]pyridin-3-yl]-2-pyrimidinamine;

N-Cyclopentyl-3-[2-(cyclopentylamino)-4-pyrimidinyl]-2-(methoxymethyl)pyrazolo[1,5-a]pyridin-7-amine;

N-Cyclopentyl-3-[2-(cyclopentylamino)-4-pyrimidinyl]-2-[3-(1-pyrrolidinyl)propyl]-pyrazolo[1,5-a]pyridin-7-amine;

N-({3-[2-(Methylsulfanyl)-4-pyrimidinyl]pyrazolo[1,5-a]pyridin-2-yl}methyl)-2-propanamine;

N-Cyclopentyl-4-{2-[(isopropylamino)methyl]pyrazolo[1,5-a]pyridin-3-yl}-2-pyrimidinamine;

N-Cyclopentyl-3-[2-(cyclopentylamino)-4-pyrimidinyl]-2-[(isopropylamino)methyl]-pyrazolo[1,5-a]pyridin-7-amine;

4-{7-Chloro-2-[3-(isopropylamine)propyl]pyrazolo[1,5-a]pyridin-3-yl}-N-cyclopentyl -2-pyrimidinamine;

N-Cyclopentyl-3-[2-(cyclopentylamino)-4-pyrimidinyl]-2-[3-(isopropylamino)propyl]-pyrazolo[1,5-a]pyridin-7-amine;

4-{7-Chloro-2-[(2-methoxyethoxy)methyl]pyrazolo[1,5-a]pyridin-3-yl}-N-cyclopentyl -2-pyrimidinamine;

3-[2-(Cyclopentylamino)-4-pyrimidinyl]-2-[(2-methoxyethoxy)methyl]-N-(2-methoxyethyl)pyrazolo[1,5-a]pyridin-7-amine;

N-Cyclopentyl-3-[2-(cyclopentylamino)-4-pyrimidinyl]-2-[(2-methoxyethoxy)-methyl]pyrazolo[1,5-a]pyridin-7-amine;

N-Cyclopentyl-4-(2-isopropylpyrazolo[1,5-a]pyridin-3-yl) pyrimidin-2-amine;

N-Cyclopentyl-3-[2-(cyclopentylamino)pyrimidin-4-yl]-2-isopropylpyrazolo[1,5-a]pyridin-7-amine;

2-Cyclopropyl-3-[2-(methylthio)pyrimidin-4-yl]pyrazolo[1,5-a]pyridine;

N-Cyclopentyl-4-(2-cyclopropylpyrazolo[1,5-a]pyridin-3-yl)pyrimidin-2-amine; and N-Cyclopentyl-3-[2-(cyclopentylamino)pyrimidin-4-yl]-2-cyclopropylpyrazolo[1,5-a]pyridin-7-amine;

and pharmaceutically acceptable salts, solvates and physiologically functional derivatives thereof.

It will be appreciated by those skilled in the art that the compounds of the present invention may also be utilized in the form of a pharmaceutically acceptable salt solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of formula (I) are in the form of the mesylate salt. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the processes for preparing pharmaceutically acceptable salts, solvates and physiologically functional derivatives of the compounds of formula (I).

Certain compounds of formula (I) and intermediates used in the processes of preparing compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from restenosis following angioplasty (RFA), viral infection, particularly by CMV and/or HHV-6 plays a pivotal role in the proliferation of the smooth muscle cells in the coronary vessel. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of conditions or diseases associated with hepatitis B or hepatitis C viruses, human papilloma virus (HPV) and HIV.

The present invention also provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the prevention of infection, the prevention of occurrence of symptoms in an infected subject, the prevention of recurrence of symptoms in an infected subject, or a decrease in severity or frequency of symptoms of viral infection, condition or disease in the subject As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of a condition or disease associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective-amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the comound of formula (I) in the preparation of a medicament for the treatment of a condition or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical composition. The pharmaceutical composition may comprise a pharmaceutically acceptable carrier or diluent. The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I) with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules (including soft-gel capsules), cachets or tablets (e.g. chewable tablets in particular for paediatric administration) each containing a predetermined amount of the active ingredient, as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations suitable for topical (e.g., dermal) or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, ganciclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir or valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) may be conveniently prepared by a process outlined in Scheme 1 below.

Scheme 1

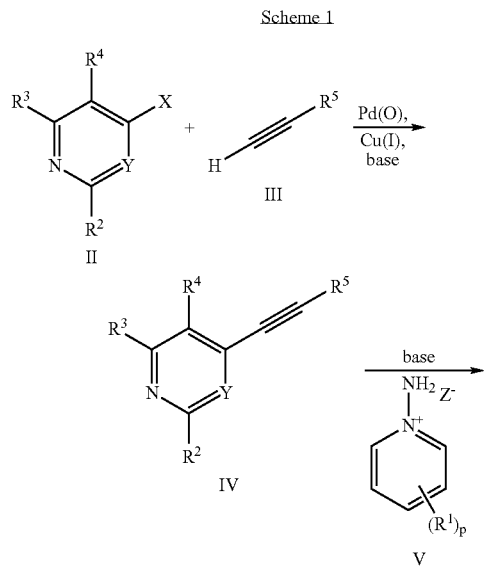

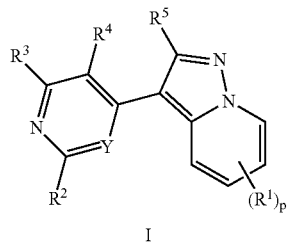

wherein X is chloro, bromo, iodo or triflate, and Z- is a counterion (e.g., a halide, sulfonate, etc.) and all other variables are as defined above.

Generally, the process for preparing a compound of formula (I) comprises the steps of:

a) coupling a compound of formula (II) to a terminal alkyne of formula (III) to prepare a compound of formula (IV); and b) reacting an N-amino pyridinium salt of formula (V) with the compound of the formula (IV) to prepare a compound of formula (I).

More specifically, a compound of formula (I) can be prepared by reacting a compound of formula (IV) with an N-amino pyridinium of formula (V).

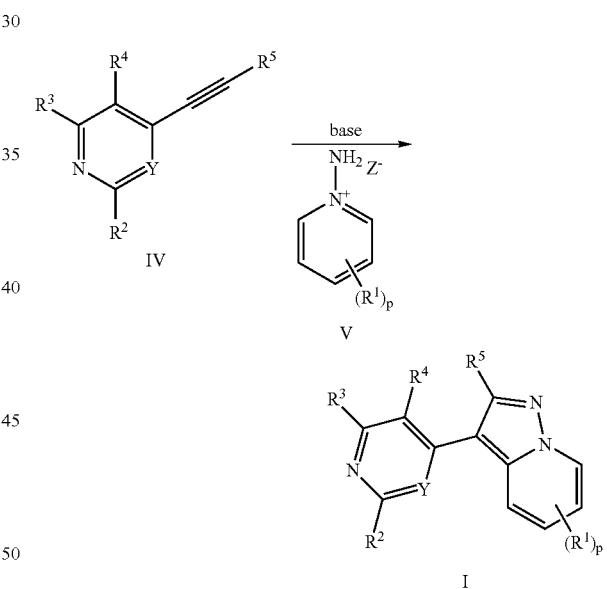

wherein all variables are as defined above.

This method can be readily carried out by mixing a compound of the formula (IV) in near equimolar amounts with a compound of formula (V) in an inert solvent in the presence of a base optionally with cooling to effect the cycloaddition reaction. Suitable solvents include but are not limited to acetonitrile, dimethyl sulfoxide, tetrahydrofuran, N,N-dimethylformamide, dioxane, 1-methyl-2-pyrrolidinone, and the lower alcohols such as methanol and ethanol. Typically the base is an amine base such as triethylamine and the like or an inorganic base such as sodium hydroxide, sodium bicarbonate, potassium carbonate, or 1,8-diazabicyclo[5.4.0]undec-7-ene (DBU) and the like. It is currently believed that the initial cycloaddition reaction produces a dihydro intermediate which is not generally observed, and which undergoes air oxidation to the aromatic compound of formula (I).

Compounds of formula (V) are aminated pyridine derivatives and are either commercially available or can be conveniently prepared by reacting a suitable pyridine with an aminating reagent such as O-(mesitylsulfonyl)hydroxylamine and the like.

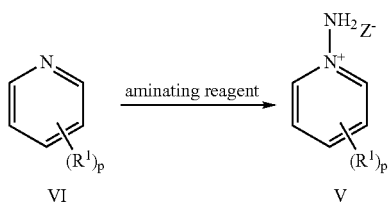

wherein all variables are as defined above.

A compound of the formula (IV) can be prepared by coupling (e.g., cross-coupling) a compound of formula (II) with a terminal alkyne of formula (III).

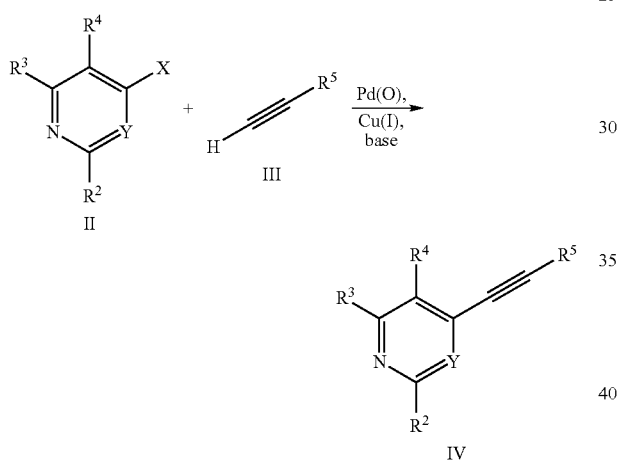

wherein all variables are as defined above.

This reaction is typically performed in an inert solvent in the presence of catalytic amounts of both a palladium (0) source and a copper (I) source along with a stoichiometric amount of base. Palladium catalysts include but are not limited to tetrakistriphenylphosphine palladium (0) and dichlorobistriphenylphosphine palladium (II). Copper (I) iodide is one source of copper co-catalyst. Typically the base is a secondary or tertiary amine such as diisopropylamine, triethylamine or diisopropylethylamine. Typical solvents are tetrahydrofuran, N,N-dimethylformamide, dioxane, and 1-methyl-2-pyrrolidinone and the like. This method is known in the art as a Sonogashira coupling. Accordingly, other catalysts, bases and solvents which can be employed for Sonogashira couplings may similarly be adapted for use in the preparation of the compounds of the present invention.

Compouds of the formula (II) are either commercially available or can be prepared according to methods known to one skilled in the art or by procedures described in the literature.

In addition to the foregoing process for preparing compounds of formula (I), the present invention also provides certain intermediate compounds for use in the preparation of such compounds of formula (I) according to the foregoing process. Such intermediates are described in connection with Scheme 1 above.

Each of the foregoing processes may further comprise the step of converting the compound of formula (I) to a pharmaceutically acceptable salt, solvate, or physiologically functional derivative thereof, using techniques well known to those skilled in the art.

As will be apparent to those skilled in the art, a compound of formula (I) or a pharmaceutically acceptable salt, solvate or physiologically functional derivative thereof may be converted to another compound of formula (I) or a pharmaceutically acceptable salt, solvate or physiologically functional derivative thereof using techniques well known in the art. For example, one method of converting a compound of formula (I) to another compound of formula (I) comprises converting a compound of formula (I-A) to a compound of formula (I-B) via a deprotonation electrophile addition reaction.

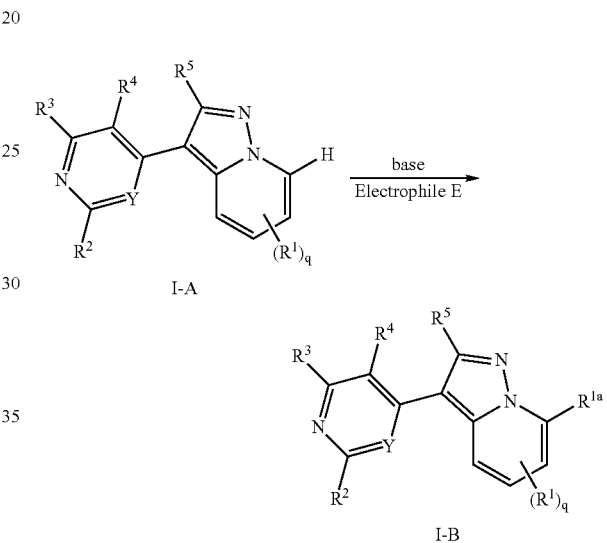

wherein q is 0, 1, or 2;

$R^1$ is as defined above and is located at the C-4, C-5 and/or C-6 position; and $R^{1a}$ is selected from halo, alkyl, —C(O)$R^9$, —C(O)Ay, —C(O)Het, —CO$_2R^9$, —C(O)NR$^7R^8$, —C(O)NR$^7$Ay, —C(O)NHR$^{10}$Het, —S(O)$_2$NR$^7R^8$, —S(O)$_2$NR$^7$Ay and —S(O)$_n R^9$; and all other variables are as defined above.

More specifically a compound of formula (I-B) can be prepared by treating a compound of formula (I-A) with a base in an inert solvent followed by the addition of an electrophilic quenching agent. Suitable bases include by way of example lithium amide bases such as lithium diisopropyl amide, and alkyllithium bases such as butyllithium. Suitable solvents include but are not limited to ether, tetrahydrofuran and the like. Electrophilic quenching reagents include but are not limited to carbon tetrachloride, hexachloroethane ($R^{1a}$=Cl), N-bromosuccinimide ($R^{1a}$=Br), and dimethyldisulfide ($R^{1a}$=—SMe).

Another particular process for converting a compound of formula (I) to another compound of formula (I) involves the deprotonation/electrophilic quench described above wherein the electrophile is B—OCH$_3$-9-borabicyclo[3.3.1]nonane (B—OMe-9-BBN. A compound of formula (I-A) thus forms upon lithiation of C7 and quenching with B—OMe-9-BBN an intermediate arylborinate of formula (VII) in situ. The aryl borinate is then able to be cross-coupled with an aryl halide in a palladium catalyzed Suzuki coupling optionally in the presence of a base to provide a compound of formula (I-C).

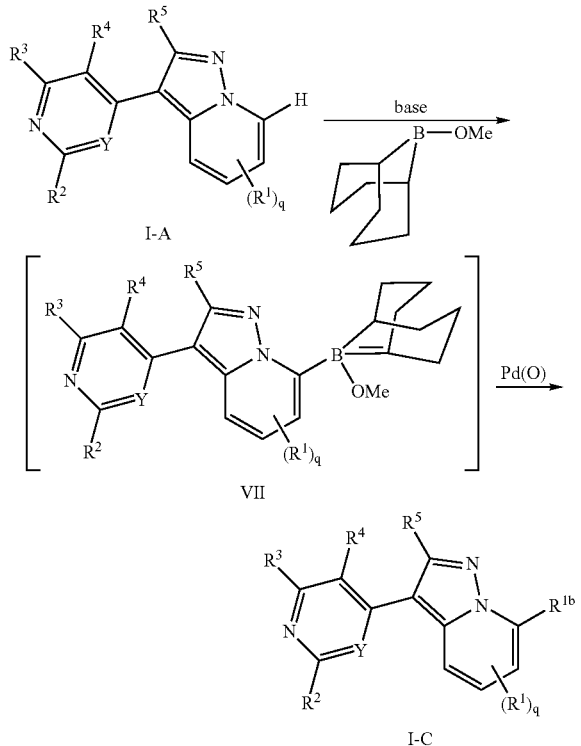

wherein:
q is 0, 1, or 2;
R¹ is as defined above and is located at the C-4, C-5 and/or C-6 position;
$R^{1b}$ is selected from Ay, Het, alkenyl, or cycloalkenyl; and
all other variables are as defined above.

As a further example, a compound of formula (I-D) can be converted to a compound of formula (I-F) by a) oxidizing the compound of formula (I-D) to prepare a compound of formula (I-E) and then b) optionally reacting a compound of formula (I-E) with an oxygen or amine nucleophile of formula $R^2$, wherein $R^2$ is selected from the group consisting of —NR⁷R⁸, —OR⁷, —OAy, Het attached through N, —NHHet, —NHR¹⁰Het, —OHet and —OR¹⁰Het to produce a compound of formula (I-F) wherein $R^2$ is selected from the group consisting of —NR⁷R⁸, —OR⁷, —OAy, Het attached through N, —NHHet, —NHR¹⁰Het, —OHet and —OR¹⁰Het.

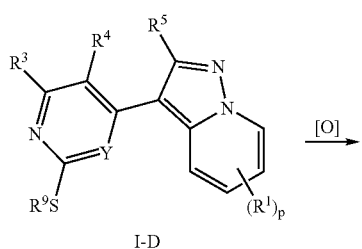

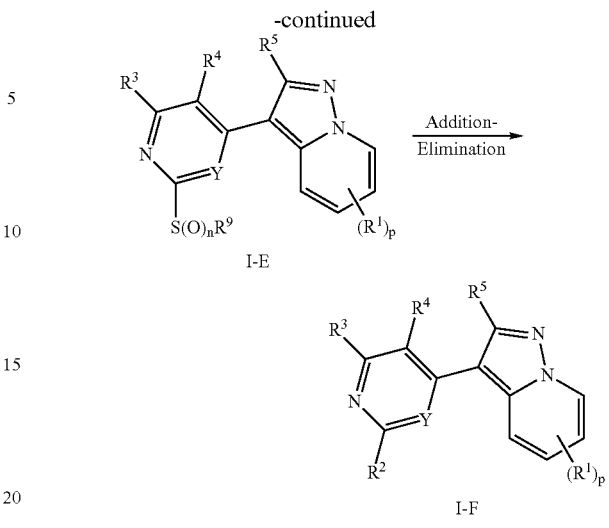

wherein n' is 1 or 2 and all other variables are as defined above.

More specifically, a compound of formula (I-F) can be prepared by reacting a compound of formula (I-E) (i.e., a compound of formula (I) wherein $R^2$ is $S(O)_{n'}R^9$ where n' is 1 or 2) with an oxygen or amine nucleophile of formula $R^2$, wherein $R^2$ is selected from the group consisting of —NR⁷R⁸, —OR⁷, —OAy, Het linked through N, —NHHet, —NHR¹⁰Het, —OHet, and —OR¹⁰Het. The reaction may be carried out neat or in a suitable solvent and may be heated to 50–150° C. Typically the solvent is a lower alcohol such as methanol, ethanol, isopropanol or the like or a solvent such as N,N-dimethylformamide or tetrahydrofuran, or the like. Optionally a base may be used to facilitate the reaction. Typically the base can be potassium carbonate, or an amine base such as triethylamine.

A compound of formula (I-E) may be conveniently prepared by reacting a compound of formula (I-D) (i.e., a compound of formula (I) wherein $R^2$ is $S(O)_nR^9$ where n is 0) with an oxidizing agent in an inert solvent, optionally in the presence of an acid or base. Typically the oxidizing agent is a peracid such as m-chloroperbenzoic acid or the like, optionally with a base such as sodium bicarbonate. If additional amines are present in the molecule, it may be desireable to perform the oxidation under acidic conditions to protect the amine from overoxidation. By way of example some specific examples of sutiable acids include acetic acid, hydrochloric acid and the like. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

A compound of formula (I-D) can be prepared by the method described above wherein $R^2=SR^9$ from the reaction of compounds selected from the group consisting of compounds of formula (IV), compounds of formula (V) prepared from compounds of formula (II) and formula (III) (i.e., the compound of formula (II) wherein $R^2$ is $SR^9$). The requisite compound of formula (II) can be obtained from commercial sources or prepared by methods known to one skilled in the art.

Another particularly useful method for converting a compound of formula (I) to a different compound of formula (I) comprises reacting a compound of formula (I-G) (i.e., a compound of formula (I) wherein $R^2$ is fluoro) with an amine, and optionally heating the mixture to 50–150° C. to prepare a compound of formula (I-H) (i.e., a compound of formula (I) wherein $R^2$ is —$NR^7R^8$).

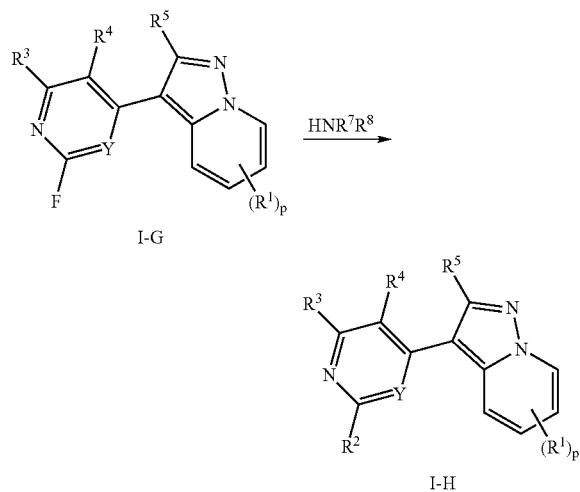

I-G

I-H wherein all variables are as defined above.

This procedure may be carried out by mixing a compound of formula (I-G) in an amine neat, or in a suitable solvent with an excess of amine to produce a compound of formula (I-H). Typically the solvent is a lower alcohol such as methanol, ethanol, isopropanol or the like. Other suitable solvents may include N,N-dimethylformamide, 1-methyl-2-pyrrolidine or the like.

As a further example, a compound of formula (I-I) may be converted to a compound of formula (I-J) using either of two methods.

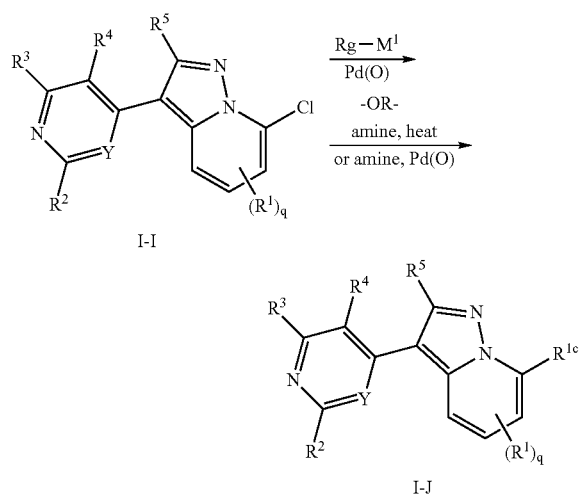

I-I

I-J wherein:
q is 0, 1 or 2;
Rg is Ay or Het;
$M^1$ is $B(OH)_2$, $B(ORa)_2$, $B(Ra)_2$, $Sn(Ra)_3$, Zn-halide, Zn—Ra or Mg-halide, where Ra is alkyl or cycloalkyl, halide is halo;
$R^{1c}$ is Ay, $NHR^{10}Ay$, —$NR^7Ay$, Het, —NHHet, and —$NHR^{10}Het$; and all other variables are as defined above.

According to one process, a compound of formula (I-I) may be converted to a compound of formula (I-J) by a process comprising replacing the C-7 halogen of the compound of formula (I-I) with an amine. Typically the replacement is carried out by mixing the compound of formula (I-I) with an amine nucleophile of formula $R^{1c}$ where $R^{1c}$ is selected from the group consisting of —$NR^7R^8$, —$NR^7Ay$, Het, —$NHR^{10}Het$, NHHet, and —$NHR^{10}Ay$; and optionally heating the reaction.

The reaction can also be carried out via an adaptation of procedures found in the literature (Wolfe, J. P.; Buchwald, S. L. J. Org. Chem. 2000, 65, 1144) wherein a compound of formula (I-I) is treated with an amine, a palladium (0) or nickel (0) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

Alternatively, a compound of formula (I-I) may be converted to a compound of formula (I-J) by a process comprising coupling the compound of formula (I-I) with a metal compound of the formula Rg-$M^1$ where $M^1$ is $B(OH)_2$, $B(ORa)_2$, $B(Ra)_2$, $Sn(Ra)_3$, Zn-halide, Zn—Ra or Mg-halide, wherein Ra is alkyl or cycloalkyl and halide is halo. This process can be conveniently performed in an inert solvent, in the presence of a palladium (0) catalyst, optionally with heating. The reaction is performed by reacting equimolar amounts of a compound of formula (I-I) with the metal compound of formula Rg-$M^1$ or optionally adding an excess of the metal compound. The palladium catalyst is preferrably present in 1–10 mol % compared to the compound of formula (I-I). Palladium catalysts that may be used may include, but are not limited to, tetrakistriphenylphosphine palladium (0) dichlorobis(triphenylphosphine)palladium(II), and bis(diphenylphosphinoferrocene)-palladium (II) dichloride. Inert solvents for use in the reaction include but are not limited to, N,N-dimethylformamide, toluene, tetrahydrofuran, dioxane, and 1-methyl-2-pyrrolidinone.

When the metal compound of formula Rg-$M^1$ is an arylboronic acid or ester or an arylborinate, the reaction is more conveniently carried out by adding a base in a proportion equivalent to, or greater than, that of the metal compound.

Metal compounds of the formula Rg-$M^1$ can be purchased from commercial sources or prepared either as discreet isolated compounds or generated in situ by using methods known to one skilled in the art. (Suzuki, A. J. Organomet. Chem. 1999, 576, 147; Stille, J. Angew. Chem. Int. Ed. Engl. 1986, 25, 508; Snieckus, V. J. Org. Chem. 1995, 60, 292.)

As further example, a compound of formula (I-K) can be converted to a compound of formula (I-L) by reductive amination.

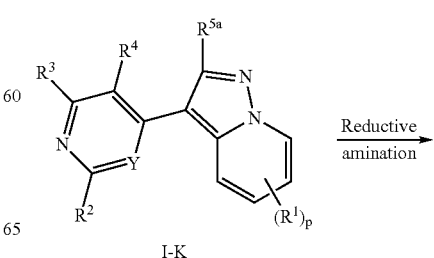

I-K

-continued

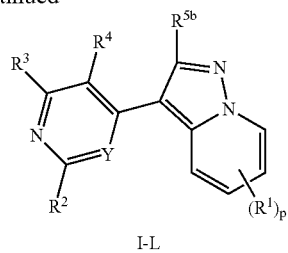

I-L wherein:
$R^{5a}$ is —C(O)$R^9$ or —$R^{10}$C(O)$R^9$;
$R^{5b}$ is —$R^{10}$Het, —$R^{10}$N$R^7R^8$, —$R^{10}$N$R^7$Ay or —$R^{10}$NHHet; and all other variables are defined above.

By way of example this process for converting a compound of formula (I-K) to a compound of formula (I-L) can be performed by treating a compound of formula (I-K) with an amine in an inert solvent with a reducing agent, optionally in the presence of an acid. Numerous techniques for reductive amination are known to those skilled in the art and can be found in the literature. This conversion may be effected using any such conventional techniques and reagents. Typical conditions include but are not limited to solvents such as 1,2-dichloroethane, dichloromethane, tetrahydrofuran, ether, methanol and the like. Reducing agents by way of example include sodium borohydride, sodium triacetoxy borohydride and sodium cyanoborohydride. The ketone or aldehyde compound of formula (I-K) may be mixed with the amine prior to addition of reducing agent to prepare an intermediate imine in-situ, followed by reduction to an amine of formula (I-L).

Another process for converting a compound of formula (I) to another compound of formula (I) involves by way of example treating a compound of formula (I-M) with an amine nucleophile selected from the group consisting of Het-H, HN$R^7R^8$, HN$R^7$Ay and NHHet, to prepare a compound of formula (I-N).

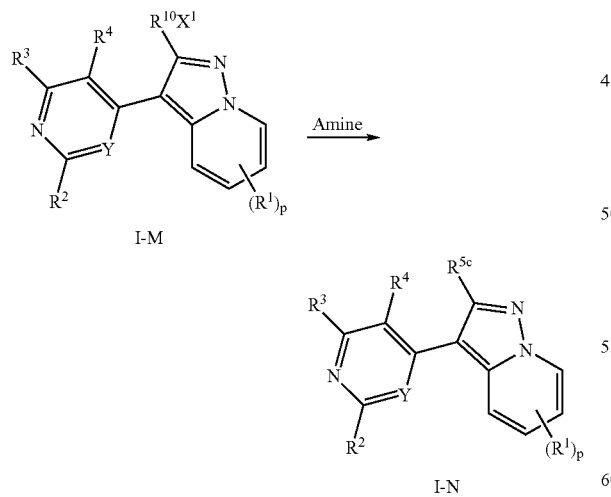

wherein:
$X^1$ is Cl, Br or iodo;
$R^{5c}$ is —$R^{10}$Het, —$R^{10}$N$R^7R^8$, —$R^{10}$N$R^7$Ay or $R^{10}$NHHet; and all other variables are as defined above.

In particular, this method can be carried out by treating a compound of formula (I-M) with an amine nucleophile neat or in an inert solvent optionally with heating. Preferred solvents include but are not limited to acetonitrile, dimethyl sulfoxide, tetrahydrofuran, N,N-dimethylformamide, dioxane, 1-methyl-2-pyrrolidinone, and the lower alcohols such as methanol, ethanol, isopropanol and the like.

In another example, a compound of formula (I-O) can be converted to a compound of formula (I-P) by a hydrolysis reaction.

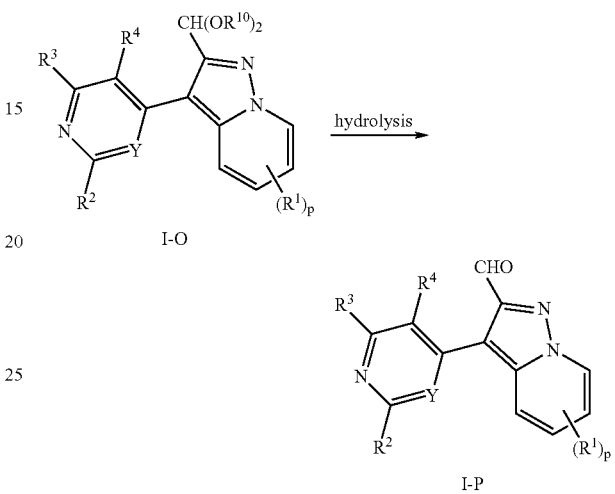

This can be performed in a biphasic or miscible solvent system which includes an aqueous component under acidic conditions. Typical solvents include but are not limited to water, tetrahydrofuran, dioxane, methanol, acetone and the like.

Another example of conversion of a compound of formula (I) to another compound of formula (I) involves the conversion of a compound of formula (I-Q) to a compound of formula (I-R) by oxidation. A compound of formula (I-Q) may be prepared by the process described in Scheme 1 above or by reaction of a compound of formula (I-P) with a suitable organo-metallic reagent, such as a Grignard reagent A compound of formula (I-Q) may further be converted to a compound of formula (I-S) by reduction.

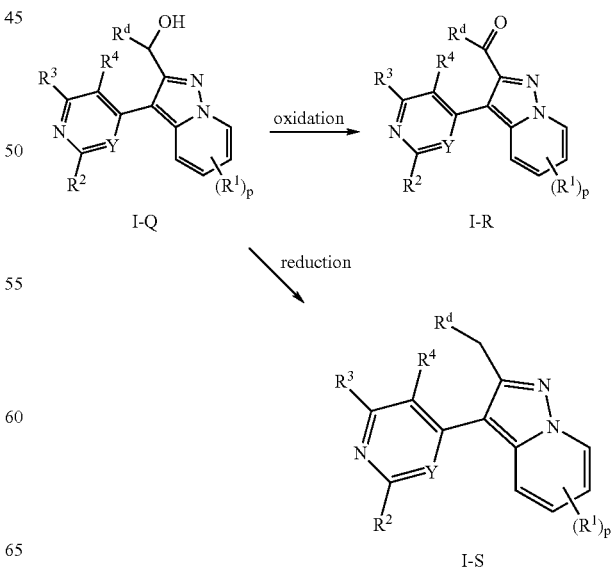

wherein:

$R^d$ is selected from H, alkyl, alkenyl, alkynyl, cycloalkyl, cycloalkenyl, —$R^{10}$cycloalkyl, —$R^{10}$Ay, —$R^{10}$Het, —$R^{10}OR^9$, —$R^{10}NR^7R^8$, —$R^{10}NR^7$Ay, —$R^{10}$NHHet, and Ay; and all other variables are defined above in connection with scheme 1.

By way of example the foregoing process of oxidizing a compound of formula (I-Q) to prepare a compound of formula (I-R) can be performed in an inert solvent in the presence of a conventional oxidant. Typical oxidants include but are not limited to manganese dioxide, and pyridinium chlorochromate and the like. Suitable solvents include but are not limited to dichloromethane, chloroform, tetrahydrofuran and the like.

In addition, a compound of formula (I-Q) can be reduced to prepare a compound of general formula (I-S) by treatment with a reducing agent in a suitable solvent. General techniques for reducing include but are not limited to catalytic hydrogenation, and hydride reagents and the like. Preferred catalytic hydrogenation conditions typically include the use of palladium on carbon in approximately 10 weight percent of substrate and an atmosphere of hydrogen at ambient or elevated pressures. Suitable solvents include but are not limited to methanol, ethanol, ethyl acetate and the like. In addition, the reduction may be accomplished through the use of hydride reagents such as lithium aluminum hydride in an ethereal solvent such as tetrahydrofuran and the like. Yet another reduction technique suitable for the conversion of a compound of formula (I-Q) to a compound of formula (I-S) involves the use of triethylsilane in the presence of boron trifluoride etherate in an inert solvent such as tetrahydrofuran or dichloromethane, and the like.

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated.

The radiolabeled compounds of formula (I) and the biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compounds of formula (I) to the target protein. More specifically, suitable assay methods will include competition binding assays. The radiolabeled compounds of formula (I) can be employed in assays according to the methods conventional in the art.

The following examples are illustrative embodiments of the invention, not limiting the scope of the invention in any way, the invention being defined by the claims which follow. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

3-(2-Fluoropyridin-4-yl)-2-propylpyrazolo[1,5-a]pyridine

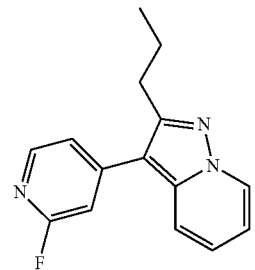

a) 2-Fluoro-4-pent-1-ynylpyridine.

To a cold (0° C.) solution of 2-fluoro-4-iodopyridine (1.0 g, 4.5 mmol) in tetrahydrofuran (15 mL) was added copper (I) iodide (86 mg, 0.45 mmol), dichlorobistriphenylphosphine palladium (II) (157 mg, 0.22 mmol), and triethylamine (1.8 mL, 13.4 mmol). Pentyne (0.88 mL, 8.9 mmol) was added dropwise to the reaction mixture and the resultant solution was stirred at 0° C. for 30 minutes and then at room temperature for 18 hours. Water and ether were added and the layers separated. The organic layer was washed with brine. The aqueous layer was extracted with ether and the combined organics were dried over magnesium sulfate. Filtration and concentration followed flash chromatography on silica gel (5:1 hexane-ether) provided 2-fluoro-4-pent-1-ynylpyridine (670 mg, 92%) as a clear oil. $^1$H NMR (CDCl$_3$) δ 8.11 (d, 1H), 7.11 (d, 1H), 6.88 (s, 1H), 2.41 (t, 2H), 1.63 (m, 2H), 1.04 (t,3H),; $^{19}$F NMR (CDCl$_3$) δ −68.68; MS m/z 164 (M+1).

b) 3-(2-Fluoropyridin-4-yl)-2-propylpyrazolo[1,5-a]pyridine.

To a cold (0° C.) solution of 2-fluoro-4-pent-1-ynylpyridine (650 mg, 3.98 mmol) in acetonitrile (15 mL) was added 1,8-diazabicyclo[5.4.0]undec-7-ene (DBU) (0.89 mL, 5.97 mmol) and 1-aminopyridinium iodide (974 mg, 4.38 mmol). The resultant dark solution was allowed to warm to room temperature and stirred vigorously. An additional equivalent of 1,8-diazabicyclo[5.4.0]undec-7-ene and 1-aminopyridinium iodide were added after 18 and again after 36 hours. Water was added and the mixture concentrated in vacuo. The residue was partitioned between water and ether. The organic layer was washed with brine. The aqueous layer was extracted with ether and the combined organics were dried over magnesium sulfate. Filtration and concentration followed flash chromatography on silica gel (4:1 to 3:1 hexane-ethyl acetate) provided 3-(2-fluoropyridin-4-yl)-2-propylpyrazolo[1,5-a]pyridine (765 mg, 75%) as an off-white solid. $^1$H NMR (CDCl$_3$) δ 8.48 (d, 1H), 8.30 (d, 1H), 7.64 (d, 1H), 7.32–7.23 (m, 2H), 7.04 (s, 1H), 6.86 (t, 1H), 2.95 (t, 2H), 1.82 (m, 2H), 1.03 (t, 3H); $^{19}$F NMR (CDCl$_3$) δ −68.48; MS m/z 256 (M+1).

EXAMPLE 2

N-Cyclopentyl-4-(2-propylpyrazolo[1,5-a]pyridin-3-yl)pyridin-2-amine

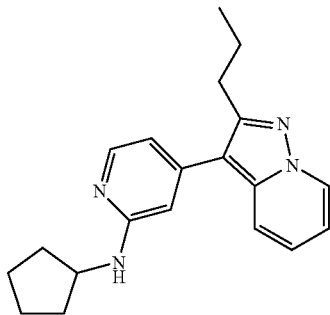

A solution of 3-(2-fluoropyridin-4-yl)-2-propylpyrazolo[1,5-a]pyridine (126 mg, 0.49 mmol) in cyclopentylamine (5 mL) was heated in a sealed vessel at 150° C. for 18 h. The mixture was cooled to room temperature and concentrated in vacuo and the residue was purified by flash chromatography on silica gel (2:1 hexane-ethyl acetate) to give N-cyclopentyl-4-(2-propylpyrazolo[1,5-a]pyridin-3-yl)pyridin-2-amine (155 mg, 98%) as a yellow solid. $^1$H NMR (CDCl$_3$) δ 8.41 (d, 1H), 8.07 (d, 1H), 7.58 (d, 1H), 7.14 (t, 1H), 6.74 (td, 1H), 6.66 (dd, 1H), 6.45 (s, 1H), 5.01 (broad, 1H), 3.95 (m, 1H), 2.91 (t, 2H), 2.04 (m, 2H), 1.80–1.50 (m, 8H), 0.98 (t, 3H); MS m/z 321 (M+1).

EXAMPLE 3

7-Chloro-3-(2-fluoropyridin-4-yl)-2-propylpyrazolo[1,5-a]pyridine

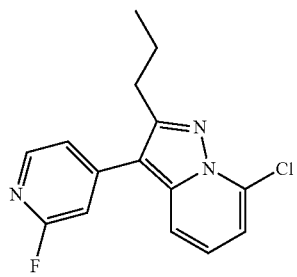

A solution of 3-(2-fluoropyridin-4-yl)-2-propylpyrazolo[1,5-a]pyridine (109 mg, 0.42 mmol) in tetrahydrofuran (5 mL) was cooled to −78° C. Butyllithium (0.4 mL, 1.6 M in hexane, 0.64 mmol) was added dropwise and the resultant solution was stirred at −78° C. for 45 minutes. Carbon tetrachloride (0.3 mL) was added and the mixture was stirred at −78° C. for 30 minutes and then quenched byt the addition of methanol while cold. Upon warming to room temperature water and ether were added and the layers separated. The organic layer was washed with brine. The aqueous layer was extracted with ether and the combined organics were dried over magnesium sulfate. Filtration and concentration followed flash chromatography on silica gel (4:1 to 2:1 hexane-ethyl acetate) provided 7-chloro-3-(2-fluoropyridin-4-yl)-2-propylpyrazolo[1,5-a]pyridine (77 mg, 63%) as an orange solid. $^1$H NMR (CDCl$_3$) δ 8.33 (d, 1H), 7.58 (d, 1H), 7.30 (m, 1H), 7.22 (t, 1H), 7.02–6.98 (m, 2H), 2.99 (t, m, 2H), 1.01 (t, 3H); $^{19}$F NMR (CDCl$_3$) δ −68.11; MS m/z 290 (M+1).

EXAMPLE 4

N-Cyclopentyl-3-[2-(cyclopentylamino)pyridin-4-yl]-2-propylpyrazolo[1,5-a]pyridin-7-amine

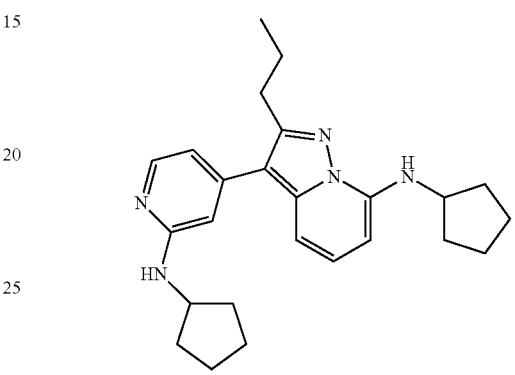

A solution of 7-chloro-3-(2-fluoropyridin-4-yl)-2-propylpyrazolo[1,5-a]pyridine (41 mg, 0.14 mmol) in cyclopentylamine (5 mL) was heated in a sealed vessel at 150° C. for 18 h. The mixture was cooled to room temperature and concentrated in vacuo and the residue was purified by flash chromatography on silica gel (2:1 hexane-ethyl acetate) to give N-cyclopentyl-3-[2-(cyclopentylamino)pyridin-4-yl]-2-propylpyrazolo[1,5-a]pyridin-7-amine (44 mg, 77%) as a yellow solid. $^1$H NMR (CDCl$_3$) δ 8.10 (d, 1H), 7.18 (t, 1H), 7.00 (d, 1H), 6.73 (d, 1H), 6.52 (s, 1H), 5.97–5.91 (m, 2H), 5.07 (m, 1H), 4.00 (m, 2H), 2.95 (t, 2H), 2.18–2.05 (m, 4H), 1.87–1.57 (m, 14H), 1.02 (t, 3H); MS m/z 404 (M+1).

EXAMPLE 5

2-Isobutyl-3-[2-(methylthio)pyrimidin-4-yl]pyrazolo[1,5-a]pyridine

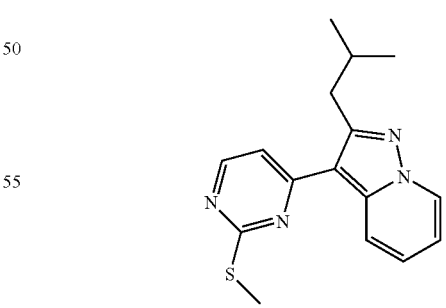

a) 4-(4-Methylpent-1-ynyl)-2-(methylthio)pyrimidine.

To a cold (0° C.) solution of 4-iodo-2-(methylthio)pyrimidine (4.73 g, 21.2 mmol) in tetrahydrofuran (70 mL) was added copper (I) iodide (404 mg, 2.12 mmol), dichlorobis-triphenylphosphine palladium (II) (744 mg, 1.06 mmol), and triethylamine (8.8 mL, 63.8 mmol). 4-Methyl-pentyne (5.0 mL, 42.5 mmol) was added dropwise to the reaction mixture and the resultant solution was stirred at 0° C. for 30 minutes and then at room temperature for 72 hours. Water and ether were added and the layers separated. The organic layer was washed with brine. The aqueous layer was extracted with ether and the combined organics were dried over magnesium sulfate. Filtration and concentration followed flash chromatography on silica gel (4:1 hexane-ether) provided 4-(4-methylpent-1-ynyl)-2-(methylthio)pyrimidine (4.0 g, 92%) as a clear oil. $^1$H NMR (CDCl$_3$) δ 8.44 (d, 1H), 6.96 (d, 1H), 2.56 (s, 3H), 2.35 (d, 2H), 1.97 (M, 1H), 1.05 (d, 6H); MS m/z 207 (M+1).

b) 2-Isobutyl-3-[2-(methylthio)pyrimidin-4-yl]pyrazolo[1,5-a]pyridine.

To a cold (0° C.) solution of 4-(4-methylpent-1-ynyl)-2-(methylthio)pyrimidine (2.5 g, 12 mmol) in acetonitrile (40 mL) was added 1,8-diazabicyclo[5.4.0]undec-7-ene (DBU) (2.7 mL, 18 mmol) and 1-aminopyridinium iodide (3.49 g, 15.7 mmol). The resultant dark solution was allowed to warm to room temperature and stirred vigorously. The mixture was heated to 50° C. for 18 h then cooled to room temperature. Water was added and the mixture concentrated in vacuo. The residue was partitioned between water and ether. The organic layer was washed with brine. The aqueous layer was extracted with ether and the combined organics were dried over magnesium sulfate. Filtration and concentration followed flash chromatography on silica gel (6:1 to 4:1 to 2:1 hexane-ethyl acetate) provided 2-isobutyl-3-[2-(methylthio)pyrimidin-4-yl]pyrazolo[1,5-a]pyridine (2.0 g, 56%) as a yellow solid. $^1$H NMR (CDCl$_3$) δ 8.51–8.48 (m, 2H), 8.36 (d, 1H), 7.35 (t, 1H), 7.19 (d, 1H), 6.91 (t, 1H), 3.04 (d, 2H), 2.68 (s, 3H), 2.20 (m, 1H), 1.03 (d, 6H); MS m/z 299 (M+1).

EXAMPLE 6

2-Isobutyl-3-[2-(methylsulfinyl)pyrimidin-4-yl]pyrazolo[1,5-a]pyridine

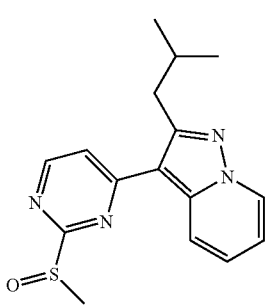

To a cold (0° C.) solution of 2-isobutyl-3-[2-(methylthio)pyrimidin-4-yl]pyrazolo[1,5-a]pyridine (890 mg, 2.98 mmol) in dichloromethane (25 mL) was added sodium bicarbonate solid (500 mg), and m-chloroperbenzoic acid (734 mg, ~70% pure, 2.98 mmol). The mixture was stirred at 0° C. for 20 minutes and then quenched by the addition of saturated aqueous sodium thiosulfate and saturated aqueous sodium bicarbonate. The biphasic mixture was allowed to warm to room temperature and stirred vigorously for 15 minutes. The layers were separated and the organic layer washed with brine. The aqueous layer was extracted with dichloromethane and the combined organics were dried over sodium sulfate. Filtration and concentration in vacuo provided 2-isobutyl-3-[2-(methylsulfinyl)pyrimidin-4-yl]pyrazolo[1,5-a]pyridine (930 mg, 99%) as a yellow solid. $^1$H NMR (CDCl$_3$) δ 8.73 (d, 1H), 8.63 (d, 1H), 8.47 (d, 1H), 7.48 (d, 1H), 7.43 (t, 1H), 6.94 (t, 1H), 3.00 (d, 2H), 2.99 (s, 3H), 2.16 (m, 1H), 1.01 (d, 6H); MS m/z 315 (M+1).

EXAMPLE 7

N-Cyclopentyl-4-(2-isobutylpyrazolo[1,5-a]pyridin-3-yl)pyrimidin-2-amine

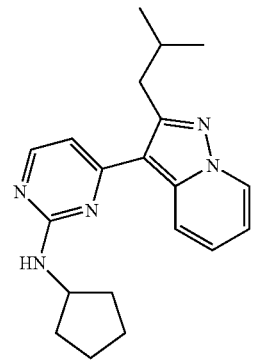

A solution of 2-isobutyl-3-[2-(methylsulfinyl)pyrimidin-4-yl]pyrazolo[1,5-a]pyridine (930 mg, 2.98 mmol) in cyclopentylamine (5 mL) was heated at 130° C. for 4 h. The mixture was cooled to room temperature and concentrated in vacuo and the residue was purified by flash chromatography on silica gel (2:1 to 1:1 hexane-ethyl acetate) to give N-cyclopentyl-4-(2-isobutylpyrazolo[1,5-a]pyridin-3-yl)pyrimidin-2-amine (890 mg, 89%) as a White solid. $^1$H NMR (CDCl$_3$) δ 8.44 (d, 1H), 8.28–8.25 (m, 2H), 7.26 (m, 1H), 6.85–6.76 (m, 2H), 5.08 (m, 1H), 4.40 (m, 1H), 3.00 (d, 2H), 2.26–2.05 (m, 3H), 1.83–1.51 (m, 6H), 1.00 (d, 6H); MS m/z 336 (M+1).

EXAMPLE 8

N-Cyclopentyl-4-[2-isobutyl-7-(methylthio)pyrazolo[1,5-a]pyridin-3-yl]pyrimidin-2-amine

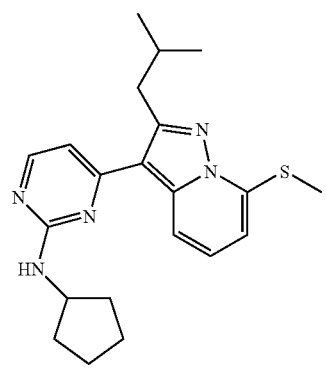

To a cold (−78° C.) solution of N-cyclopentyl-4(2-isobutylpyrazolo[1,5-a]pyridin-3-yl)pyrimidin-2-amine (750 mg, 2.23 mmol) in tetrahydrofuran (25 mL) was added lithium diisopropylamide (LDA) (11.18 mL of a 0.6 M stock solution was prepared from 18.75 mL of 1.6 M butyllithium and 4.20 mL of diisopropylamine in 27 mL of tetrahydrofuran, 6.71 mmol) dropwise. The reusitant solution was stirred at −78° C. for 15 minutes. Dimethyldisulfide (1.0 mL, 11.15 mmol) was added rapidly and the mixture was stirred for 1 hour. Water and ether were added and the layers separated. The organic layer was washed with brine. The aqueous layer was extracted with ether and the combined organics were dried over magnesium sulfate. Filtration and concentration followed flash chromatography on silica gel (2:1 hexane-ether) provided N-cyclopentyl-4-[2-isobutyl-7-(methylthio)pyrazolo[1,5-a]pyridin-3-yl]pyrimidin-2-amine. (712 mg, 84%) as a yellow solid. $^1$H NMR (CDCl$_3$) δ 8.25 (d, 1H), 8.07 (d, 1H), 7.25 (t, 1H), 6.75 (d, 1H), 6.61 (d, 1H), 5.04 (d, 1H), 4.37 (m, 1H), 3.05 (d, 2H), 2.61 (s, 3H), 2.26–2.05 (m, 3H), 1.79–1.50 (m, 6H), 0.97 (d, 6H); MS m/z 382 (M+1).

EXAMPLE 9

N-Cyclopentyl-4-[2-isobutyl-7-(methylsulfinyl)pyrazolo[1,5-a]pyridin-3-yl]pyrimidin-2-amine

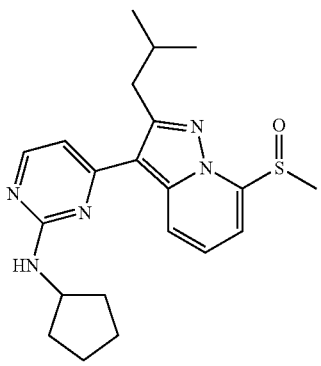

To a cold (0° C.) solution of N-cyclopentyl-4-[2-isobutyl-7-(methylthio)pyrazolo[1,5-a]pyridin-3-yl]pyrimidin-2-amine (700 mg, 1.83 mmol) in dichloromethane (30 mL) was added sodium bicarbonate solid (500 mg), and m-chloroperbenzoic acid (451 mg, ~70% pure, 1.83 mmol). The mixture was stirred at 0° C. for 20 minutes and then quenched by the addition of saturated aqueous sodium thiosulfate and saturated aqueous sodium bicarbonate. The biphasic mixture was allowed to warm to room temperature and stirred vigorously for 15 minutes. The layers were separated and the organic layer washed with brine. The aqueous layer was extracted with dichloromethane and the combined organics were dried over sodium sulfate. Filtration and concentration in vacuo provided N-cyclopentyl-4-[2-isobutyl-7-(methylsulfinyl)pyrazolo[1,5-a]pyridin-3-yl]pyrimidin-2-amine (720 mg, 99%) as a yellow solid. $^1$H NMR (CDCl$_3$) δ 8.38–8.29 (m, 2H), 7.51–7.44 (m, 2H), 6.77 (d, 1H), 5.24 (m, 1H), 4.38 (m, 1H), 3.13 (s, 3H), 3.08–2.91 (m, 2H), 2.25–2.05 (m, 3H), 1.82–1.54 (m, 6H), 0.98 (m, 6H); MS m/z 398 (M+1).

EXAMPLE 10

N-Cyclopentyl-3-[2-(cyclopentylamino)pyrimidin-4-yl]-2-isobutylpyrazolo[1,5-a]pyridin-7-amine

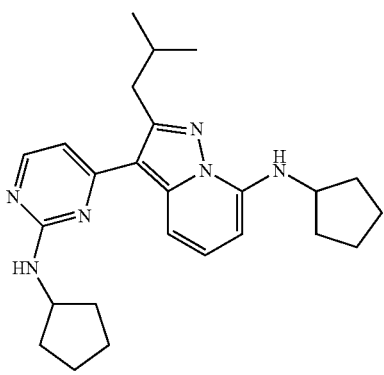

A solution of N-cyclopentyl-4-[2-isobutyl-7-(methylsulfinyl)pyrazolo[1,5-a]pyridin-3-yl]pyrimidin-2-amine (110 mg, 0.28 mmol) in cyclopentylamine (5 mL) was heated at 130° C. for 72 h. The mixture was cooled to room temperature and concentrated in vacuo and the residue was purified by flash chromatography on silica gel (hexane-ethyl acetate) to give N-cyclopentyl-3-[2-(cyclopentylamino)pyrimidin-4-yl]-2-isobutylpyrazolo[1,5-a]pyridin-7-amine (93 mg, 81%) as a White solid. $^1$H NMR (CDCl$_3$) δ 8.20 (d, 1H), 7.50 (d, 1H), 7.21 (t, 1H), 6.74 (d, 1H), 5.97–5.92 (m, 2H), 5.09 (d, 1H), 4.38 (m, 1H), 3.96 (m, 1H), 3.01 (d, 2H), 2.27–2.04 (m, 5H), 1.81–1.50 (m, 12H), 0.97 (d, 6H); MS m/z 419 (M+1).

EXAMPLE 11

2-(Diethoxymethyl)-3-[2-(methylthio)pyrimidin-4-yl]pyrazolo[1,5-a]pyridine

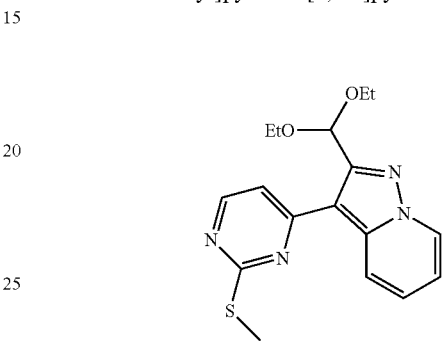

The title compound was prepared in a similar manner to those described above to give a tinted oil. $^1$H NMR (CDCl$_3$) δ 8.57–8.47 (m, 3H), 7.79 (d, 1H), 7.34 (t, 1H), 6.92 (t, 1H), 5.92 (s, 1H), 3.80–3.62 *m, 4H), 2.64 (s, 3H), 1.23 (t, 6H); MS m/345 (M+1).

EXAMPLE 12

3-[2-(Methylthio)pyrimidin-4-yl]pyrazolo[1,5-a]pyridine-2-carbaldehyde

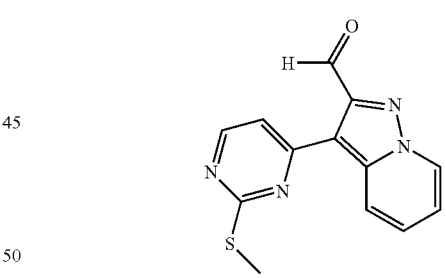

A solution of 2-(diethoxymethyl)-3-[2-(methylthio)pyrimidin-4-yl]pyrazolo[1,5-a]pyridine (1.3 g, 3.8 mmol) in tetrahydrofuran (20 mL) was treated with aqueous hydrochloric acid (10 mL 4 M), the resultant solution was stirred for 18 h. The solvents were removed in vacuo and the residue was taken up in dichloromethane and the pH adjusted to >7 with 1N aqueous sodium hydroxide. The organic layer was washed with brine. The aqueous layer was extracted with dichloromethane and the combined organics were dried over sodium sulfate. Filtration and concentration followed flash chromatography on silica gel (1:1 to 1:2 hexane-ethyl acetate) provided 3-[2-(Methylthio)pyrimidin-4-yl]pyrazolo[1,5-a]pyridine-2-carbaldehyde (804 mg, 790%) as a yellow solid. $^1$H NMR (CDCl$_3$) δ 10.42 (s, 1H), 8.61–8.58 (m, 3H), 7.92 (d, 1H), 7.44 (m, 1H), 7.12 (m, 1H), 2.65 (s, 3H); MS m/z 271 (M+1).

EXAMPLE 13

{3-[2-(methylthio)pyrimidin-4-yl]pyrazolo[1,5-a]pyridin-2-yl}(phenyl)methanol

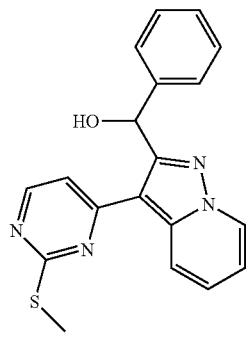

To a cold (−78° C.) solution of 3-[2-(methylthio)pyrimidin-4-yl]pyrazolo[1,5-a]pyridine-2-carbaldehyde (520 mg, 1.92 mmol) in tetrahydrofuran (40 mL) was added phenylmagnesium bromide (2.88 mL 1.0 M in tetrahydrofuran, 2.88 mmol). The reaction was warmed to 0° C. and stirred for 1 hour. The reaction mixture was then recooled to −78° C. and additional phenylmagnesium bromide (2.00 mL, 1.0 M in tetrahydrofuran, 2.00 mmol) was added and stirred at room temperature for 14 hours. The reaction was quenched with water and the resulting mixture was concentrated in vacuo to remove the excess tetrahydrofuran. The resulting aqueous mixture was extracted with dichloromethane. The organic layer was washed with water and dried over magnesium sulfate. Filtration and concentration, followed by flash chromatography (49:1 dichloromethane:methanol) provided {3-[2-(methylthio)pyrimidin-4-yl]pyrazolo[1,5-a]pyridin-2-yl}(phenyl)methanol (550 mg, 82%) as a white solid. $R_f$ 0.31 (49:1 dichloromethane:methanol); $^1$H NMR (CDCl$_3$) δ 8.52 (d, 1H), 8.40 (d, 1H), 7.87 (d, 1H), 7.43–7.13 (m, 7H), 6.93 (t, 1H), 6.21 (s, 1H), 2.60 (s, 3H); MS m/349 (M+1).

EXAMPLE 14

{3-[2-(Cyclopentylamino)-4-pyrimidinyl]pyrazolo[1,5-a]pyridin-2-yl}(phenyl)methanol

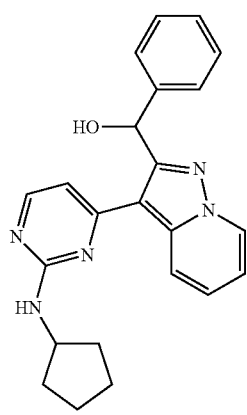

To a cold (0° C.) solution of {3-[2-(methylthio)pyrimidin-4-yl]pyrazolo[1,5-a]pyridin-2-yl}(phenyl)methanol (294 mg, 0.844 mmol) in dichloromethane (30 mL) was added m-chloroperoxybenzoic acid (218 mg, 1.26 mmol). The reaction mixture was stirred for 1.5 hours at 0° C., then diluted with dichloromethane and washed with saturated aqueous sodium bicarbonate solution. The organic layer was dried over magnesium sulfate, then filtered and concentrated. The resulting solid was heated in cyclopentylamine (2 mL, 20 mmol) at 45° C. for 16 hours. Concentration and flash chromatography (59:1 dichloromethane:methanol) provided {3-[2-(cyclopentylamino)-4-pyrimidinyl]pyrazolo[1,5-a]pyridin-2-yl}(phenyl)methanol (120 mg, 89%) as a light yellow solid. $R_f$ 0.55 (29:1 dichloromethane:methanol); $^1$H NMR (CDCl$_3$) δ 8.50 (d, 1H), 8.22 (d, 1H), 7.96 (br, 1H), 7.82 (d, 1H), 7.40 (d, 2H), 7.35–7.17 (m, 4H), 6.85 (t, 1H), 6.78 (d, 1H), 6.20 (s, 1H), 5.12 (s, 1H), 4.29 (m, 1H), 2.05 (m, 2H), 1.79–1.60 (m, 4H), 1.49 (m, 2H); MS m/z 386 (M+1).

EXAMPLE 15

{3-[2-(Cyclopentylamino)-4-pyrimidinyl]pyrazolo[1,5-a]pyridin-2-yl}(phenyl)methanone

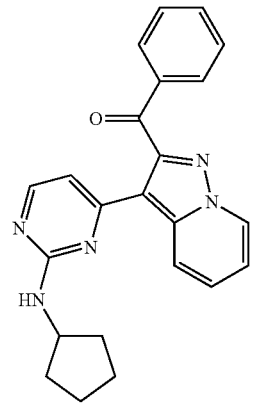

To a solution of {3-[2-(cyclopentylamino)-4-pyrimidinyl]pyrazolo[1,5-a]pyridin-2-yl}(phenyl)methanol (227 mg, 0.589 mmol) in chloroform (10 mL) was added manganese dioxide (454 mg, 5.22 mmol). The reaction mixture was stirred for 2 days at room temperature. The reaction mixture was diluted with dichloromethane and filtered through a pad of celite. The filtrate was concentrated to provide {3-[2-(cyclopentylamino)-4-pyrimidinyl]pyrazolo[1,5-a]pyridin-2-yl}(phenyl)methanone (200 mg, 89%) as a white solid. $R_f$ 0.30 (1:1 hexanes:ethyl acetate); $^1$H NMR (CDCl$_3$) δ 8.58 (d, 1H), 8.40 (d, 1H), 8.16 (d, 1H), 8.00 (d, 2H), 7.61 (t, 1H), 7.55–7.38 (m, 3H), 7.01 (t, 1H), 6.75 (d, 1H), 5.02 (d, 1H), 4.18 (m, 1H), 1.96 (m, 2H), 1.70–1.41 (m, 6H); MS m/z 384 (M+1).

EXAMPLE 16

{7-(Cyclopentylamino)-3-[2-(cyclopentylamino)-4-pyrimidinyl]-pyrazolo[1,5-a]pyridin-2-yl}(phenyl)methanone

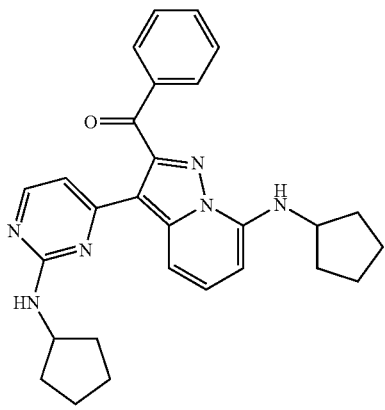

The title compound was prepared in a similar manner to those described above to give a Yellow solid; $R_f$ 0.44 (3:2 hexanes:ethyl acetate); $^1$H NMR (CDCl$_3$) δ 8.11 (d, 1H), 7.98 (d, 2H), 7.51 (d, 2H), 7.49–7.38 (m, 3H), 6.70 (d, 1H), 6.10 (d, 1H), 6.01 (d, 1H), 4.89 (d, 1H), 4.04–3.96 (m, 2H), 2.12 (m, 2H), 1.94–1.15 (m, 14H); MS m/z 467 (M+1).

EXAMPLE 17

4-(2-Benzylpyrazolo[1,5-a]pyridin-3-yl)-N-cyclopentyl-2-pyrimidinamine

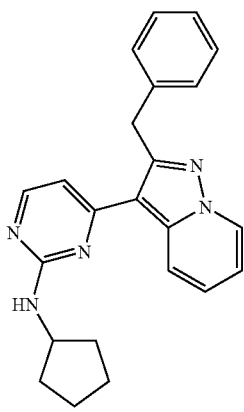

To a solution of concentrated sulfuric acid (9 mL, 169 mmol) in ethanol (25 mL) was added 10% palladium on carbon (200 mg) and a solution of {3-[2-(cyclopentylamino)-4-pyrimidinyl]pyrazolo[1,5-a]pyridin-2-yl}(phenyl)methanol (350 mg, 0.908 mmol) in ethanol (5 mL). The reaction mixture was stirred under 55 PSI of hydrogen for 3 days. The reaction mixture was filtered through a pad of celite. Saturated aqueous sodium bicarbonate solution was added to the filtrate until basic. The resulting mixture was concentrated on rotovap to remove the excess ethanol, then extracted with ethyl acetate. The organic layer was washed with water and brine, then dried over magnesium sulfate. Filtration and concentration, followed by flash chromatography (29:1 dichloromethane:methanol) provided 4-(2-benzylpyrazolo[1,5-a]pyridin-3-yl)-N-cyclopentyl-2-pyrimidinamine (221 mg, 66%) as an off-white solid. $^1$H NMR (CDCl$_3$) δ 8.45 (d, 1H), 8.25 (d, 1H), 8.19 (d, 1H), 7.30–7.13 (m, 6H), 6.82 (m, 1H), 6.63 (d, 1H), 5.12 (d, 1H), 4.52 (s, 2H), 4.35 (m, 1H), 2.03 (m, 2H), 1.78–1.50 (m, 6H); MS m/z 370 (M+1).

EXAMPLE 18

4-(2-Benzyl-7-chloropyrazolo[1,5-a]pyridin-3-yl)-N-cyclopentyl-2-pyrimidinamine

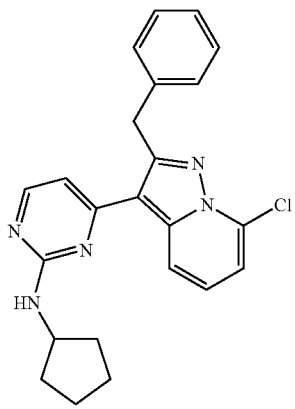

To a cold (−78° C.) solution of 4-(2-benzylpyrazolo[1,5-a]pyridin-3-yl)-N-cyclopentyl-2-pyrimidinamine (207 mg, 0.560 mmol) in tetrahydrofuran (7 mL) was added lithium diisopropylamide (17.5 mL, 0.16 M in tetrahydrofuran, 2.80 mmol). The reaction mixture was stirred at −78° C. for 45 minutes, then carbon tetrachloride (542 μl, 5.60 mmol) was added. The reaction mixture was stirred for an additional 30 minutes at −78° C. The reaction mixture was quenched with water, warmed to room temperature, and extracted with ethyl acetate. The organic layer was washed with water and brine, then dried over magnesium sulfate. Filtration and concentration, followed by flash chromatography (4:1 hexanes:ethyl acetate) provided 4-(2-benzyl-7-chloropyrazolo[1,5-a]pyridin-3-yl)-N-cyclopentyl-2-pyrimidinamine (60 mg, 27%) as a yellow solid. $^1$H NMR (CDCl$_3$) δ 8.35 (d, 1H), 8.21 (d, 1H), 7.35–7.16 (m, 6H), 7.04 (d, 1H), 6.64 (d, 1H), 5.20 (d, 1H), 4.60 (s, 2H), 4.37 (m, 1H), 2.09 (m, 2H), 1.82–1.48 (m, 6H); MS m/z 404 (M+1).

EXAMPLE 19

N-{4-[2-Benzyl-7-(cyclopentylamino)pyrazolo[1,5-a]pyridin-3-yl]-2-pyrimidinyl}-N-cyclopentylamine

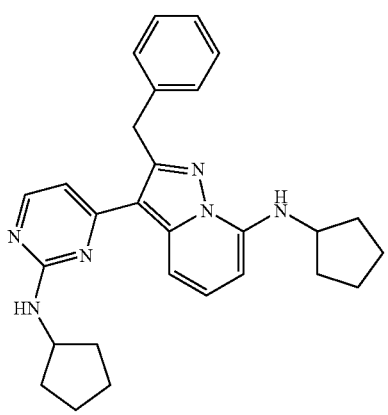

A solution of 4-(2-benzyl-7-chloropyrazolo[1,5-a]pyridin-3-yl)-N-cyclopentyl-2-pyrimidinamine (65 mg, 0.16 mmol) in cyclopentylamine (2 mL, 20 mmol) was heated at 116° C. for 16 hours. The reaction mixture was cooled and the excess cyclopentylamine was removed in vacuo. The crude material was chromatographed (19:1 dichloromethane:acetone) to provide N-{4-[2-benzyl-7-(cyclopentylamino)pyrazolo[1,5-a]pyridin-3-yl]-2-pyrimidinyl}-N-cyclopentylamine (23 mg 32%) as a pale yellow solid. $R_f$ 0.12 (5:1 hexanes:ethyl acetate); $^1$H NMR δ 8.18 (d, 1H), 7.59 (d, 1H), 7.30–7.10 (m, 6H), 6.65 (d, 1H), 5.99 (d, 1H), 4.59 (s, 2H), 4.30 (m, 1H), 3.98 (m, 1H), 2.21–2.00 (m, 4H), 1.90–1.50 (m, 12H); MS m/z 453 (M+1).

EXAMPLE 20

N-Cyclopentyl-4-[2-(methoxymethyl)pyrazolo[1,5-a]pyridin-3-yl]-2-pyrimidinamine

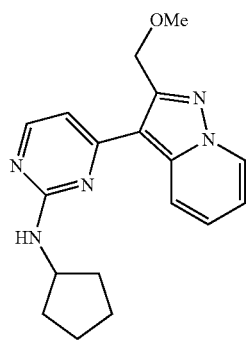

The title compound was prepared in a similar manner to those described above to give a tan solid; $R_f$ 0.32 (1:1 hexanes:ethyl acetate); $^1$H NMR δ 8.49 (d, 1H), 8.40 (d, 1H), 8.30 (d, 1H), 7.30 (t, 1H), 6.99 (d, 1H), 6.90 (t, 1H), 5.21 (d, 1H), 4.90 (s, 2H), 4.39 (m, 1H), 3.50 (s, 3H), 2.12 (m, 2H), 1.82–1.50 (m, 6H); MS m/z 324 (M+1).

EXAMPLE 21

N-Cyclopentyl-4-[2-(methoxymethyl)-7-(methylsulfanyl)pyrazolo[1,5-a]pyridin-3-yl]-2-pyrimidinamine

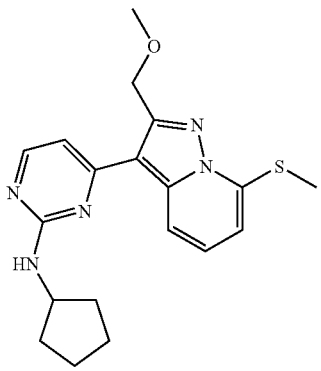

The title compound was prepared in a similar manner to those described above to give a green solid; $R_f$ 0.26 (1:1 hexanes:ethyl acetate); $^1$H NMR (CDCl$_3$) δ 8.38–8.28 (m, 2H), 7.31 (m, 1H), 7.08 (d, 1H), 6.70 (d, 1H), 5.21 (d, 1H), 4.90 (s, 2H), 4.39 (m, 1H), 3.50 (s, 3H), 2.65 (s, 3H), 2.15 (m, 2H), 1.85–1.50 (m, 6H); MS m/z 370 (M+1).

EXAMPLE 22

N-Cyclopentyl-3-[2-(cyclopentylamino)-4-pyrimidinyl]-2-(methoxymethyl)pyrazolo[1,5-a]pyridin-7-amine

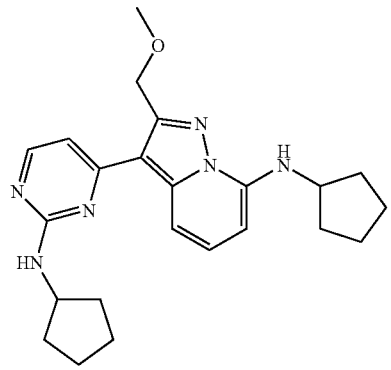

The title compound was prepared in a similar manner to those described above to give a yellow solid; $R_f$ 0.21 (2:1 hexanes:ethyl acetate); $^1$H NMR (CDCl$_3$) δ 8.23 (d, 1H), 7.65 (d, 1H), 7.29 (m, 1H), 6.05–5.95 (m, 2H), 5.15 (d, 1H), 4.89 (s, 2H), 4.40 (m, 1H), 3.99 (m, 1H), 3.51 (s, 3H), 2.20–2.02 (m, 4H), 1.90–1.50 (m, 12H); MS m/z 407 (M+1).

EXAMPLE 23

N-Cyclopentyl-3-[2-(cyclopentylamino)-4-pyrimidinyl]-2-[3-(1-pyrrolidinyl)propyl]pyrazolo[1,5-a]pyridin-7-amine

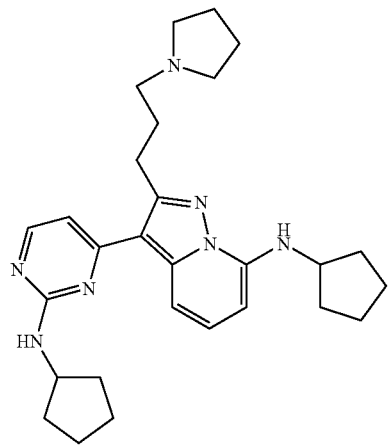

The title compound was prepared in a similar manner to those described above to give a brown solid; $^1$H NMR (CDCl$_3$) δ 8.24 (d, 1H), 7.51 (d, 1H), 7.29 (m, 1H), 6.80 (d, 1H), 6.04–5.98 (m, 2H), 5.18 (d, 1H), 4.40 (m, 1H), 4.03 (m, 1H), 3.24 (t, 2H), 3.38–3.62 (br, 6H), 2.35–2.10 (m, 6H), 2.00–1.55 (m, 12); MS m/z 474 (M+1).

EXAMPLE 24

N-({3-[2-(Methylsulfanyl)-4-pyrimidinyl]pyrazolo[1,5-a]pyridin-2-yl}methyl)-2-propanamine

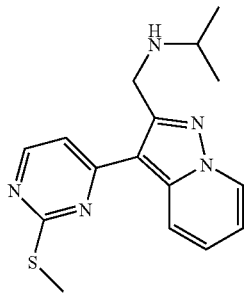

The title compound was prepared in a similar manner to those described above to give a yellow solid; $^1$H NMR (CDCl$_3$) δ 8.52–8.48 (m, 2H), 8.16 (d, 1H), 7.41–7.34 (m, 2H), 6.95 (t, 1H), 4.35 (s, 2H), 3.07 (m, 1H), 2.62 (s, 3H), 1.25 (d, 6H); MS m/z 314 (M+1).

EXAMPLE 25

N-Cyclopentyl-4-{2-[(isopropylamino)methyl]pyrazolo[1,5-a]pyridin-3-yl}-2-pyrimidinamine

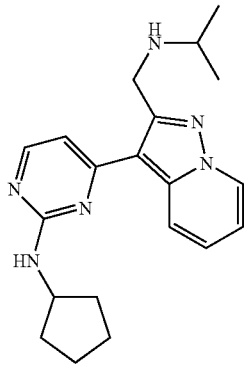

The title compound was prepared in a similar manner to those described above to give a beige solid; R$_f$ 0.50 (47:3 dichloromethane:methanol); $^1$H NMR (CDCl$_3$) δ 8.42 (d, 1H), 8.25 (d, 1H), 8.19 (d, 1H), 7.23 (m, 1H), 6.90 (d, 1H), 6.76 (t, 1H), 5.30 (br, 1H), 4.35 (m, 1H), 4.20 (s, 2H), 2.90 (m, 1H), 2.07 (m, 2H), 1.80–1.42 (m, 6H), 1.10 (d, 6H); MS m/z 351 (M+1).

EXAMPLE 26

N-Cyclopentyl-3-[2-(cyclopentylamino)-4-pyrimidinyl]-2-[(isopropylamino)methyl]pyrazolo[1,5-a]pyridin-7-amine

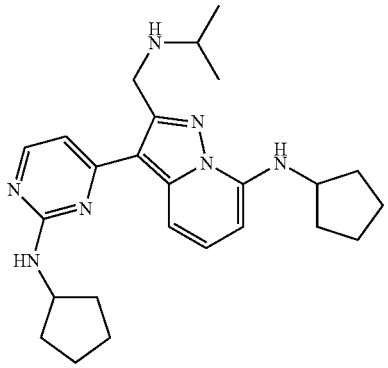

The title compound was prepared in a similar manner to those described above to give a brown solid. $^1$H NMR (CDCl$_3$) δ 11.30 (br, 1H), 8.40 (d, 1H), 7.41 (t, 1H), 7.25 (m, 2H), 6.89 (d, 1H), 6.15 (d, 1H), 6.02 (d, 1H), 4.52 (s, 2H), 4.36 (m, 1H), 4.02 (m, 1H), 2.99 (br, 1H), 2.22–1.95 (m, 4H), 1.95–1.55 (m, 12H), 1.42 (d, 6H); MS m/z 434 (M+1).

EXAMPLE 27

4-{7-Chloro-2-[3-(isopropylamino)propyl]pyrazolo[1,5-a]pyridin-3-yl}-N-cyclopentyl-2-pyrimidinamine

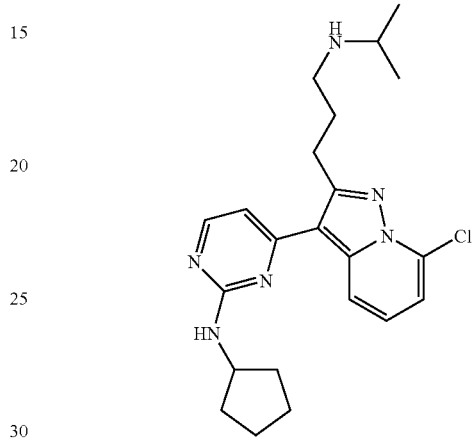

The title compound was prepared in a similar manner to those described above to give a tan solid. $^1$H NMR (CDCl$_3$) δ 8.31 (d, 1H), 8.20 (d, 1H), 7.20 (t, 1H), 6.98 (d, 1H), 6.80 (d, 1H), 5.29 (br, 1H), 4.38 (m, 1H), 3.22 (t, 2H), 2.79 (m, 1H), 2.70 (t, 2H), 2.15–1.98 (m, 4H), 1.80–1.50 (m, 6H), 1.04 (d, 6H); MS m/z 413 (M+1).

EXAMPLE 28

N-Cyclopentyl-3-[2-(cyclopentylamino)-4-pyrimidinyl]-2-[3-(isopropylamino)propyl]pyrazolo[1,5-a]pyridin-7-amine

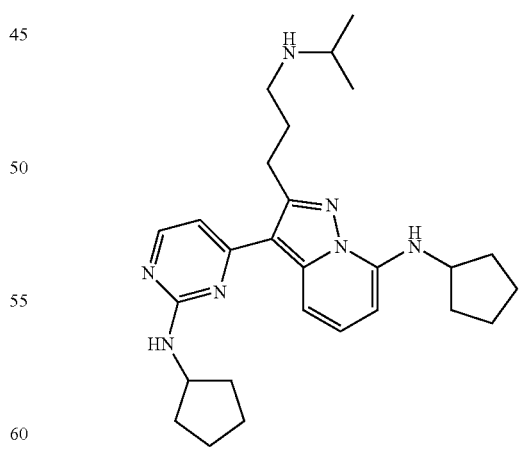

The title compound was prepared in a similar manner to those described above to give a brown oil. $^1$H NMR (CDCl$_3$) δ 8.26 (d, 1H), 7.50 (d, 1H), 7.30 (d, 1H), 6.80 (d, 1H), 6.02–5.95 (m, 2H), 5.20 (br, 1H), 4.40 (m, 1H), 4.01 (m, 1H), 3.22 (t, 2H), 2.80 (m, 1H), 2.70 (t, 2H), 2.21–1.98 (m, 6H), 1.98–1.50 (m, 12H), 1.07 (d, 6H); MS m/z 462 (M+1).

EXAMPLE 29

4-{7-Chloro-2-[(2-methoxyethoxy)methyl]pyrazolo[1,5-a]pyridin-3-yl}-N-cyclopentyl-2-pyrimidinamine

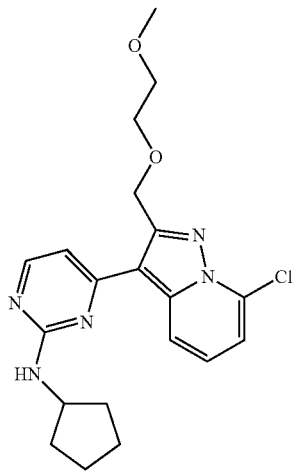

The title compound was prepared in a similar manner to those described above to give a tan solid; $^1$H NMR (CDCl$_3$) δ 8.50 (d, 1H), 8.35 (d, 1H), 7.27 (d, 1H), 7.20 (d, 1H), 7.03 (d, 1H), 5.21 (d, 1H), 4.98 (s, 2H), 4.38 (m, 1H), 3.78 (m, 2H), 3.58 (m, 2H), 3.37 (s, 3H), 2.09 (m, 2H), 1.80–1.49 (m, 6H); MS m/z 402 (M+1).

EXAMPLE 30

3-[2-(Cyclopentylamino)-4-pyrimidinyl]-2-[(2-methoxyethoxy)methyl]-N-(2-methoxyethyl)pyrazolo[1,5-a]pyridin-7-amine

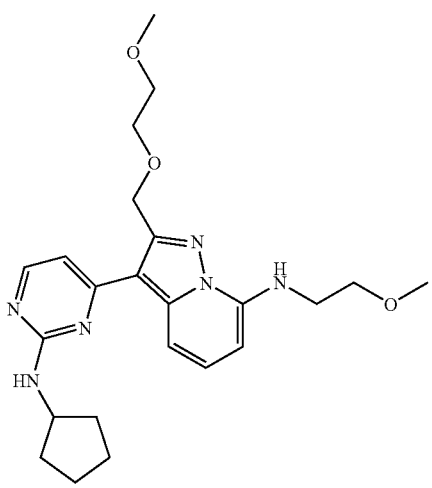

The title compound was prepared in a similar manner to those described above to give a yellow oil; $^1$H NMR (CDCl$_3$) δ 8.27 (d, 1H), 7.76 (d, 1H), 7.30 (m, 1H), 7.10 (d, 1H), 6.32 (t, 1H), 6.02 (d, 1H), 5.18 (d, 1H), 5.00 (s, 2H), 4.41 (m, 1H), 3.81–3.70 (m, 4H), 3.62–3.50 (m, 4H), 3.46 (s, 3H), 3.41 (s, 3H), 2.15 (m, 2H), 1.83–1.52 (m, 6H), MS m/z 441 (M+1).

EXAMPLE 31

N-Cyclopentyl-3-[2-(cyclopentylamino)-4-pyrimidinyl]-2-[(2-methoxyethoxy)methyl]pyrazolo[1,5-a]pyridin-7-amine

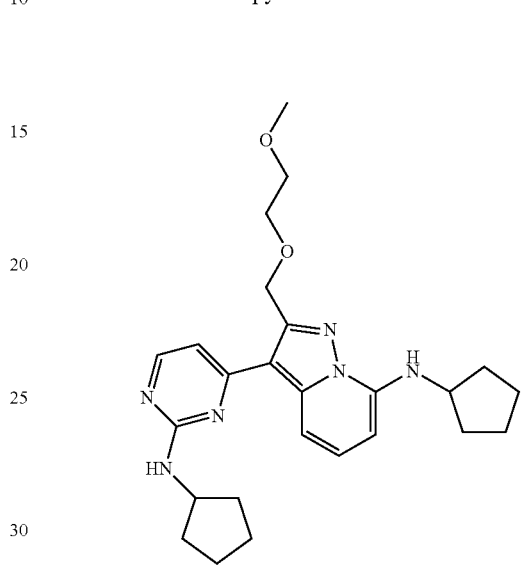

The title compound was prepared in a similar manner to those described above to give a yellow solid; $^1$H NMR (CDCl$_3$) δ 8.29 (d, 1H), 7.64 (d, 1H), 7.30 (t, 1H), 7.09 (d, 1H), 6.09–5.99 (m, 2H), 5.20 (d, 1H), 5.00 (s, 2H), 4.41 (m, 1H), 4.00 (m, 1H), 3.80 (m, 2H), 3.62 (m, 2H), 3.41 (s, 3H), 2.22–2.02 (m, 4H), 1.95–1.50 (m, 12H); MS m/z 451 (M+1).

EXAMPLE 32

N-Cyclopentyl-4-(2-isopropylpyrazolo[1,5-a]pyridin-3-yl)pyrimidin-2-amine

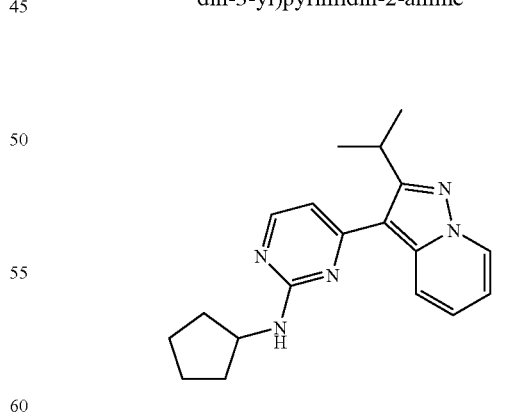

The title compound was prepared in a similar manner as described above to give a brown solid. $^1$H NMR (CDCl$_3$) δ: 8.46 (d, 1H), 8.28 (d, 1H), 8.15 (d, 1H), 7.23 (m, 1H), 6.84–6.76 (m, 2H), 5.08 (d, 1H), 4.38 (m, 1H), 2.14–2.04 (m, 4H), 1.89–1.53 (m, 4H), 1.45 (d, 6H); MS m/z 322 (M+1).

EXAMPLE 33

N-Cyclopentyl-3-[2-(cyclopentylamino)pyrimidin-4-yl]-2-isopropylpyrazolo[1,5-a]pyridin-7-amine

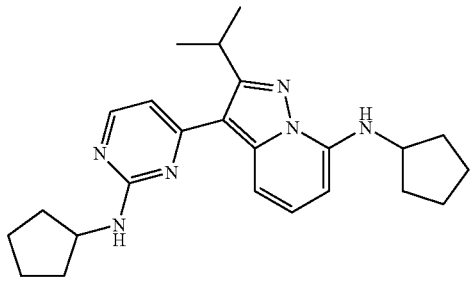

The title compound was prepared in a similar manner as described above to give a brown solid. $^1$H NMR (CDCl$_3$) δ: 8.16 (d, 1H), 7.41 (d, 1H), 7.21 (d, 1H), 6.76 (d, 1H), 6.00, (d, 1H), 5.93 (d, 1H), 4.37 (m, 1H), 3.95 (m, 1H), 2.134–2.04 (3H, m), 1.83–1.62 (m, 8H), 1.41 (d, 6H), 1.30–1.22 (m, 5H); MS m/z 405 (M+1).

EXAMPLE 34

2-Cyclopropyl-3-[2-(methylthio)pyrimidin-4-yl]pyrazolo[1,5-a]pyridine

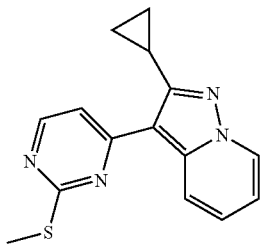

The title compound was prepared in a similar manner as described above to give a yellow solid. $^1$H NMR (CDCl$_3$) δ: 8.50–8.39 (m, 3H), 7.54 (d, 1H), 7.30 (m, 1H), 6.87 (m, 1H), 2.67 (s, 3H), 2.31 (m, 1H), 1.16 (m, 4H); MS m/z 283 (M+1).

EXAMPLE 35

N-Cyclopentyl-4-(2-cyclopropylpyrazolo[1,5-a]pyridin-3-yl)pyrimidin-2-amine

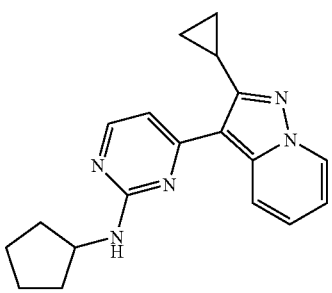

The title compound was prepared in a similar manner as described above to give a tan solid. $^1$H NMR (CDCl$_3$) δ: 8.36 (d, 2H), 8.27 (d, 1H), 7.23 (m, 1H), 7.10 (d, 1H), 6.79 (m, 1H), 5.06 (d, 1H), 4.38 (m, 1H), 2.36 (m, 1H), 2.13–2.07 (m, 2H), 1.80–1.53 (m, 6H), 1.18–1.06 (m, 4H); MS m/z 320 (M+1)

EXAMPLE 36

N-Cyclopentyl-3-[2-(cyclopentylamino)pyrimidin-4-yl]-2-cyclopropylpyrazolo[1,5-a]pyridin-7-amine

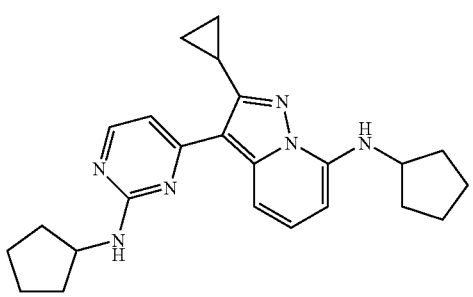

The title compound was prepared in a similar manner as described above to give a yellow solid. $^1$H NMR (CDCl$_3$) δ: 8.22 (d, 1H), 7.66 (d, 1H), 7.23 (m, 1H), 7.08 (d, 1H), 5.93 (d, 1H), 5.87 (d, 1H), 5.09 (d, 1H), 4.39 (m, 1H), 3.95 (m, 1H), 2.43 (m, 1H), 2.14–2.07 (m, 4H), 1.88–1.50 (m, 12H), 1.15 (m, 2H), 1.07 (m, 2H); MS m/z 403 (M+1)

EXAMPLE 37

Biological Activity

In the following example, "MEM" means Minimal Essential Media; "FBS" means Fetal Bovine-Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180

μM dTP, 20 μM dUTP-digoxigenin (Boehringer Mannheim 1558706), 200 μM each of dATP, dCTP, and dGTP, 1×PCR Buffer II (Perkin Elmer), 2.5 mM MgCl$_2$, 0.025 units/μL of AmpliTaq Gold polymerase (Perkin Elmer), and 5 ng of gel-purified HSV DNA per 100 μL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5× Denhardt's solution, 0.25×APE, and 5 ng of the digoxigenin-labeled detection probe). APE is 1.5 M NH$_4$-acetate, 0.15 M ammonium phosphate monobasic, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | IC$_{50}$ (μM) |
| --- | --- |
| 1 | >40 |
| 2 | 8 |
| 3 | 37 |
| 4 | 0.9 |
| 5 | 21 |
| 6 | 24 |
| 7 | 18 |
| 8 | 3.8 |
| 9 | 1.9 |
| 10 | 0.5 |
| 12 | >5 |
| 14 | 2.5 |
| 15 | 7 |
| 16 | 0.4 |
| 17 | 2 |

-continued

| Example No. | IC$_{50}$ (μM) |
| --- | --- |
| 19 | 0.8 |
| 20 | 15 |
| 21 | 4.6 |
| 22 | 1.2 |
| 23 | >2.5 |
| 24 | 2.1 |
| 25 | 27 |
| 26 | >2.5 |
| 27 | 23 |
| 28 | >5 |
| 29 | 23 |
| 30 | 4.7 |
| 31 | 1.5 |
| 32 | 4.4 |
| 33 | 2 |
| 34 | >40 |
| 35 | 3.1 |
| 36 | 0.9 |

The results demonstrate that the compounds of the present invention are useful for the treatment and prophylaxis of herpes viral infections.

The invention claimed is:

1. A compound of formula (I):

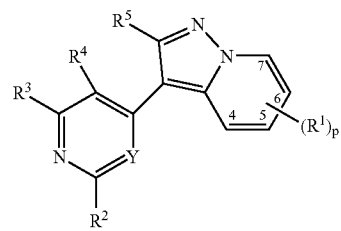

wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, —OR$^7$, —OAy, —OR$^{10}$Ay, —OHet, —OR$^{10}$Het, —C(O)R$^9$, —C(O)Ay, —C(O)Het, —CO$_2$R$^9$, —C(O)NR$^7$R$^8$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$O—C(O)R$^9$, —R$^{10}$O—C(O)Ay, —R$^{10}$O—C(O)Het, —R$^{10}$O—S(O)$_n$R$^9$, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_n$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or
two adjacent $R^1$ groups together with the atoms to which they are bonded form a C$_{5-6}$cycloalkyl or a 5 or 6-membered heterocyclic ring containing 1 or 2 heteroatoms;
each $R^7$ and $R^8$ are the same or different and are independently selected from the group consisting of H, alkyl, alkenyl, cycloalkyl, cycloalkenyl, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$;

each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

$R^2$ is selected from the group consisting of halo, alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay;

n is 0, 1 or 2;

Y is N;

$R^3$ and $R^4$ are the same or different and are each independently selected from the group consisting of H, halo, alkyl, alkenyl, cycloalkyl, Ay, Het, —$OR^7$, —OAy, —$C(O)R^7$, —C(O)Ay, —$CO_2R^7$, —$CO_2$Ay, —$SO_2NHR^9$, —$NR^7R^8$, —$NR^7$Ay, —NHHet, —$NHR^{10}$Het,—$R^{10}$cycloalkyl, —$R^{10}OR^7$, —$R^{10}$OAy, —$R^{10}NR^7R^8$ and —$R^{10}NR^7$Ay;

$R^5$ is the selected from the group consisting of H, halo, alkyl, alkenyl, alkynyl, cycloalkyl, cycloalkenyl, —$OR^7$, —OAy, —OHet, —$OR^{10}$Ay, —$OR^{10}$Het, —$C(O)R^9$, —C(O)Ay, —C(O)Het, —$CO_2R^9$, —C(O)NR^7R^8$, —C(O)NR^7$Ay, —$C(O)NHR^{10}$Het, —CH$(OR^9)_2$, —CH$(OR^9)$—$R^{10}$, —CH$(OR^9)$—Ay, —C(S)NR^9R^{11}$, —C(NH)NR^7R^8$, —C(NH)NR^7$Ay, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}OR^9$, —$R^{10}C(O)R^9$, —$R^{10}C(O)$Ay, —$R^{10}C(O)$Het, —$R^{10}CO_2R^9$, —$R^{10}C(O)NR^9R^{11}$, —$R^{10}C(O)NR^7$Ay, —$R^{10}C(O)NHR^{10}$Het, —$R^{10}CH(OR^9)$—$R^{10}$, —$R^{10}CH(OR^9)$—Ay, —$R^{10}C(S)NR^9R^{11}$, —$R^{10}C(NH)NR^9R^{11}$, —$R^{10}SO_nR^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or or a pharmaceutically acceptable salt thereof.

2. The compound according to claim 1 wherein each $R^1$ is the same or different and is independently selected from the group consisting of halo, alkyl, cycloalkyl, Ay, Het, —$OR^7$, —$C(O)R^9$, —C(O)Het, —$CO_2R^9$, —$C(O)NR^7R^8$, —C(O)NR^7Ay$, —$C(O)NHR^{10}$Het, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)NR^7$Ay, —$R^{10}SO_2NHCOR^9$, —$R^{10}NR^7R^8$, —$R^{10}NR^7$Ay, cyano, nitro and azido.

3. The compound according to claim 1 wherein each $R^1$ is the same or different and is independently selected from the group consisting of halo, Ay, Het, —$NR^7R^8$ and —$NR^7$Ay.

4. The compound according to claim 1 wherein p is 0 or 1.

5. The compound according to claim 1 wherein $R^2$ is selected from the group consisting of halo, alkenyl, cycloalkyl, cycloalkenyl, Ay, Het, —$OR^7$, —OAy, —OHet, —$OR^{10}$Het, —$S(O)_nR^9$, —$NR^7R^8$, —NHHet, —$NHR^{10}$Het, —$R^{10}NR^7R^8$ and —$R^{10}NR^7$Ay.

6. The compound according to claim 1 wherein $R^2$ is —$NR^7R^8$.

7. The compound according to claim 1 wherein $R^3$ and $R^4$ are the same or different and are each independently selected from the group consisting of H, halo, alkyl, Ay, —$OR^7$, —$CO_2R^7$, —$NR^7R^8$, —$R^{10}OR^7$ and —$R^{10}NR^7R^8$.

8. The compound according to claim 1 wherein $R^3$ and $R^4$ are both H.

9. The compound according to claim 1 wherein $R^5$ is selected from the group consisting of halo, alkyl, cycloalkyl, —$OR^7$, —$C(O)R^9$, —C(O)Ay, —C(O)Het, —CH$(OR^9)$—$R^{10}$, —CH$(OR^9)$—Ay, —$S(O)_nR^9$, —$S(O)_2NR^7R^8$, —$NR^7R^8$, —$NR^7$Ay, —$R^{10}$cycloalkyl, —$R^{10}$Ay, —$R^{10}OR^9$, —$R^{10}C(O)R^9$, —$R^{10}SO_2NR^9R^{11}$ and —$R^{10}NR^7R^8$.

10. The compound according to claim 1, wherein $R^5$ is selected from the group consisting of alkyl, —C(O)Ay, —CH$(OR^9)$—Ay, —$R^{10}$cycloalkyl, —$R^{10}$Ay, —$R^{10}OR^9$ and —$R^{10}NR^7R^8$.

11. A compound selected from the group consisting of:
2-Isobutyl-3-[2-(methylthio)pyrimidin-4-yl]pyrazolo[1,5-a]pyridine;
2-Isobutyl-3-[2-(methylsulfinyl)pyrimidin-4-yl]pyrazolo[1,5-a]pyridine;
N-Cyclopentyl-4-(2-isobutylpyrazolo[1,5-a]pyridin-3-yl)pyrimidin-2-amine;
N-Cyclopentyl-4-[2-isobutyl-7-(methylthio)pyrazolo[1,5-a]pyridin-3-yl]pyrimidin-2-amine;
N-Cyclopentyl-4-[2-isobutyl-7-(methylsufinyl)pyrazolo[1,5-a]pyridin-3-yl]pyrimidin-2-amine;
N-Cyclopentyl-3-[2-(cyclopentylamino)pyrimidin-4-yl]-2-isobutylpyrazolo[1,5-a]pyridin-7-amine;
2-(Diethoxymethyl)-3-[2-(methylthio)pyrimidin-4-yl]pyrazolo[1,5-a]pyridine;
3-[2-(Methylthio)pyrimidin-4-yl]pyrazolo[1,5-a]pyridine-2-carbaldehyde;
{3-[2-(methylthio)pyrimidin-4-yl]pyrazolo[1,5-a]pyridin-2-yl}(phenyl)methanol;
{3-[2-(Cyclopentylamino)-4-pyrimidinyl]pyrazolo[1,5-a]pyridin-2-yl}(phenyl)methanol;
{3-[2-(Cyclopentylamino)-4-pyrimidinyl]pyrazolo[1,5-a]pyridin-2-yl}(phenyl)methanone;
{7-(Cyclopentylamino)-3-[2-(cyclopentylamino)-4-pyrimidinyl]pyrazolo[1,5-a]pyridin-2-yl}(phenyl)methanone;
4-(2-Benzylpyrazolo[1,5-a]pyridin-3-yl)-N-cyclopentyl-2-pyrimidinamine;
4-(2-Benzyl-7-chloropyrazolo[1,5-a]pyridin-3-yl)-N-cyclopentyl-2-pyrimidinamine;
N-{4-[2-Benzyl-7-(cyclopentylamino)pyrazolo[1,5-a]pyridin-3-yl]-2-pyrimidinyl}-N-cyclopentylamine;
N-Cyclopentyl-4-[2-(methoxymethyl)pyrazolo[1,5-a]pyridin-3-yl]-2-pyrimidinamine;
N-Cyclopentyl-4-[2-(methoxymethyl)-7-(methylsulfanyl)pyrazolo[1,5-a]pyridin-3-yl]-2-pyrimidinamine;
N-Cyclopentyl-3-[2-(cyclopentylamino)-4-pyrimidinyl]-2-(methoxymethyl)pyrazolo[1,5-a]pyridin-7-amine;
N-Cyclopentyl-3-[2-(cyclopentylamino)-4-pyrimidinyl]-2-[3-(1-pyrrolidinyl)propyl]-pyrazolo[1,5-a]pyridin-7-amine;
N-({3-[2-(Methylsulfanyl)-4-pyrimidinyl]pyrazolo[1,5-a]pyridin-2-yl}methyl)-2-propanamine;
N-Cyclopentyl-4-{2-[(isopropylamino)methyl]pyrazolo[1,5-a]pyridin-3-yl}-2-pyrimidinamine;

N-Cyclopentyl-3-[2-(cyclopentylamino)-4-pyrimidinyl]-2-[(isopropylamino)methyl]-pyrazolo[1,5-a]pyridin-7-amine;

4-{7-Chloro-2-[3-(isopropylamino)propyl]pyrazolo[1,5-a]pyridin-3-yl}-N-cyclopentyl-2-pyrimidinamine;

N-Cyclopentyl-3-[2-(cyclopentylamino)-4-pyrimidinyl]-2-[3-(isopropylamino)propyl]-pyrazolo[1,5-a]pyridin-7-amine;

4-{7-Chloro-2-[(2-methoxyethoxy)methyl]pyrazolo[1,5-a]pyridin-3-yl}-N-cyclopentyl-2-pyrimidinamine;

3-[2-(Cyclopentylamino)-4-pyrimidinyl]-2-[(2-methoxyethoxy)methyl]-N-(2-methoxyethyl)pyrazolo[1,5-a]pyridin-7-amine;

N-Cyclopentyl-3-[2-(cyclopentylamino)-4-pyrimidinyl]-2-[(2-methoxyethoxy)-methyl]pyrazolo[1,5-a]pyridin-7-amine;

N-Cyclopentyl-4-(2-isopropylpyrazolo[1,5-a]pyridin-3-yl)pyrimidin-2-amine;

N-Cyclopentyl-3-[2-(cyclopentylamino)pyrimidin-4-yl]-2-isopropylpyrazolo[1,5-a]pyridin-7-amine;

2-Cyclopropyl-3-[2-(methylthio)pyrimidin-4-yl]pyrazolo[1,5-a]pyridine;

N-Cyclopentyl-4-(2-cyclopropylpyrazolo[1,5-a]pyridin-3-yl)pyrimidin-2-amine; and N-Cyclopentyl-3-[2-(cyclopentylamino)pyrimidin-4-yl]-2-cyclopropylpyrazolo[1,5-a]pyridin-7-amine;

or a pharmaceutically acceptable salt, solvate or physiologically functional derivative thereof.

12. A pharmaceutical composition comprising a compound according to claim 1.

13. The pharmaceutical composition according to claim 12 further comprising a pharmaceutically acceptable carrier or diluent.

14. The pharmaceutical composition according to claim 12, further comprising an antiviral agent selected from the group consisting of aciclovir and valaciclovir or a pharmaceutically acceptable salt thereof.

15. A method for the treatment of a herpes viral infection selected from herpes simplex virus 1 and herpes simplex virus 2 in an animal, said method comprising administering to the animal a therapeutically effective amount of a compound according to claim 1.

16. A method for the treatment of a condition or disease associated with a herpes viral infection selected from herpes simplex virus 1 and herpes simplex virus 2 in an animal, comprising administering to the animal a therapeutically effective amount of a compound according to claim 1.

17. A process for preparing a compound according to claim 1 wherein $R^2$ is selected from —$NR^7R^8$, Het, —$NHR^{10}$Het and —NHHet and $R^3$ and $R^4$ are the same or different and are each independently H or alkyl, said process comprising the steps of:

a) coupling a compound of formula (II):

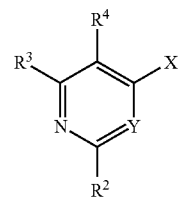

II wherein X is chloro, bromo, iodo or triflate;
$R^2$ is selected from —$NR^7R^8$, Het, —$NHR^{10}$Het and —NHHet and
$R^3$ and $R^4$ are the same or different and are each independently H or alkyl;

to a terminal alkyne of formula (III):

III to prepare a compound of formula (IV):

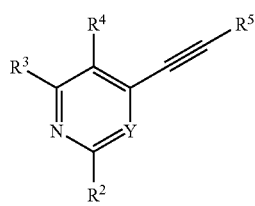

IV and b) reacting an N-amino pyridinium salt of formula (V):

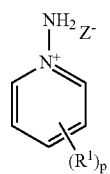

V wherein Z- is a counterion;
with the compound of the formula (IV) to prepare a compound of formula (I).

* * * * *

UNITED STATES PATENT AND TRADEMARK OFFICE
CERTIFICATE OF CORRECTION

PATENT NO. : 7,153,863 B2  Page 1 of 1
APPLICATION NO. : 10/530101
DATED : December 26, 2006
INVENTOR(S) : Gudmundsson et al.

It is certified that error appears in the above-identified patent and that said Letters Patent is hereby corrected as shown below:

Title Page

Reads;
Item (56) Foreign Patent Documents
-- WO EP 0 364 204 A1 10/1989--

Should read:
Item (56) Foreign Patent Documents
-- EP 0 364 204 A1 10/1989--

Claim 11, Column 52, line 32 reads:
"N-Cyclopentyl-4-[2-isobutyl-7- (methylsufinyl)pyrazolo"

Should read:
--N-Cyclopentyl-4-[2-isobutyl-7- (methylsulfinyl)pyrazolo--

Claim 11, Column 53, line 29:
"or a pharmaceutically acceptable salt, solvate or physic- "

Should read:
--or a pharmaceutically acceptable salt thereof. --

Signed and Sealed this

Fourth Day of September, 2007

JON W. DUDAS
*Director of the United States Patent and Trademark Office*